US012673045B2

(12) United States Patent
Vessey et al.

(10) Patent No.: US 12,673,045 B2
(45) Date of Patent: Jul. 7, 2026

(54) TREATMENT OF OCULAR DISEASE

(71) Applicant: PREMARK PHARMA GMBH, Reinach (CH)

(72) Inventors: Ian Vessey, Reinach (CH); Friedrich K. Mayer, Oberwil (CH)

(73) Assignee: PREMARK PHARMA GMBH, Reinach (CH)

( * ) Notice: Subject to any disclaimer, the term of this patent is extended or adjusted under 35 U.S.C. 154(b) by 927 days.

(21) Appl. No.: 17/612,889

(22) PCT Filed: May 20, 2020

(86) PCT No.: PCT/EP2020/064136
§ 371 (c)(1),
(2) Date: Nov. 19, 2021

(87) PCT Pub. No.: WO2020/234389
PCT Pub. Date: Nov. 26, 2020

(65) Prior Publication Data
US 2022/0218675 A1 Jul. 14, 2022

(30) Foreign Application Priority Data

May 21, 2019 (EP) .................................... 19175616

(51) Int. Cl.
| | |
|---|---|
| *A61K 31/436* | (2006.01) |
| *A61K 47/14* | (2017.01) |
| *A61P 27/02* | (2006.01) |

(52) U.S. Cl.
CPC ............ *A61K 31/436* (2013.01); *A61K 47/14* (2013.01); *A61P 27/02* (2018.01)

(58) Field of Classification Search
CPC .... A61K 31/436; A61K 47/14; A61K 31/352; A61K 31/439; A61K 9/06; A61K 47/12; A61K 47/44; A61P 27/02
See application file for complete search history.

(56) References Cited

U.S. PATENT DOCUMENTS

| | | | |
|---|---|---|---|
| 6,004,973 | A | 12/1999 | Guitard et al. |
| 6,197,781 | B1 | 3/2001 | Guitard et al. |

FOREIGN PATENT DOCUMENTS

| | | | | |
|---|---|---|---|---|
| CN | 1674868 | A | 9/2005 | |
| EP | 0 427 680 | B1 | 5/1991 | |
| EP | 1482936 | | 10/2006 | |
| EP | 1 754 482 | A1 | 2/2007 | |
| EP | 2 197 461 | A1 | 6/2010 | |
| EP | 2319493 | | 5/2011 | |
| EP | 2319493 | A2 * | 5/2011 | ........... A61K 31/195 |
| WO | WO 97/03654 | | 2/1997 | |
| WO | WO 99/01458 | | 1/1999 | |
| WO | WO 01/60345 | | 8/2001 | |
| WO | WO 01/90110 | | 11/2001 | |
| WO | WO 2004/009056 | A1 | 1/2004 | |
| WO | WO 2006/117132 | | 11/2006 | |
| WO | WO2009/048929 | | 4/2009 | |
| WO | WO 2017/152027 | | 9/2017 | |
| WO | WO 2019/033119 | | 2/2019 | |

OTHER PUBLICATIONS

De Villiers, M. (2008). Ointment bases. Pract Guide Contemp Pharm Pract, 3, 277-290 (Year: 2008).*
Russian Office Action mailed Dec. 1, 2022 accompanied by English language translation.
K. Lindsley et al., "Interventions for chronic blepharitis," *Cochrane Database of Systematic Reviews*, 2012, Issue 5, pp. 1-117.
J. M. Dougherty et al., "Comparative bacteriology of chronic blepharitis," *British Journal of Ophthalmology*, 1984, 68, pp. 524-528.
J. G. Meingassner et al., "A novel anti-inflammatory drug, SDZ ASM 981, for the topical and oral treatment of skin diseases: *in vivo pharmacology,*" *British Journal of Dermatology*, 1997, 137, pp. 568-576.
T. Zuberbier et al., "The ascomycin macrolactam pimecrolimus (Elidel, SDZ ASM 981) is a potent inhibitor of mediator release from human dermal mast cells and peripheral blood basophils," *J. Allergy Clin. Immunol.*, Aug. 2001, vol. 108, No. 2, pp. 275-280.
T. Luger et al., "SDZ ASM 981: an emerging safe and effective treatment for atopic dermatitis," *British Journal of Dermatology*, 2001, 144, pp. 788-794.
J. G. Meingassner et al., "Pimecrolimus Inhibits the Elicitation Phase but Does Not Suppress the Sensitization Phase in Murine Contact Hypersensitivity, in Contrast to Tacrolimus and Cyclosporine A[1]," *The Journal of Investigative Dermatology*, vol. 121, No. 1, Jul. 2003, pp. 77-80.
C. Auw-Hädrich et al., "Therapeutische Optionen bei chronischer Blepharitis unter Berücksichtigung der Evidenzlage," *Ophthalmologe* 2016, 12, 113, pp. 1082-1085.
B. D. Gaynor et al., "Topical ocular antibiotics induce bacterial resistance at extraocular sites," *British Journal of Ophthalmology*, 2005, 89, pp. 1097-1099.
J. D. Nelson et al., *The Ocular Surface*, 15, (2017) pp. 269-275.
M. A. Lemp et al., "Blepharitis in the United States 2009: A Survey-based Perspective on Prevalence and Treatment," *The Ocular Surface*, Apr. 2009, vol. 7, No. 2, Supplement pp. S1-S14.
Ville Kiski et al., "Long-term Safety of Topical Pimecrolimus and Topical Tacrolimus in Atopic Blepharoconjunctivitis," *JAMA Dermatology*, May 2014, vol. 150, No. 5, pp. 571-573.
G. W. Ousler, III et al., "Evaluation of Pimecrolimus 1%, 0.3% and 0.1% Compared to Vehicle for the Treatment of Dry Eye in the Controlled Adverse Environment," *The Ocular Surface*, vol. 2, No. 1, Jan. 2005, pp. S99.

(Continued)

*Primary Examiner* — James H Alstrum-Acevedo
*Assistant Examiner* — Chantal Adlam
(74) *Attorney, Agent, or Firm* — Buscher Patent PLLC

(57) ABSTRACT

The present invention is in the field of ocular disease therapy. In particular, the invention relates to a composition comprising pimecrolimus for use in the topical treatment of moderate to severe blepharitis, in particular in a patient group comprising subjects with a clinical diagnosis of moderate to severe blepharitis, wherein the subjects to be treated have signs and symptoms of moderate to severe blepharitis characterised by swelling of the eyelid margin, ocular debris and ocular discomfort. In particular, the present invention relates to an ophthalmic composition that shows a high patient acceptance and a clinically meaningful improvement in the signs and symptoms of treated patients.

16 Claims, 10 Drawing Sheets

(56) References Cited

OTHER PUBLICATIONS

J. M. Rynerson et al., "DEBS—a unification theory for dry eye and blepharitis," *Clinical Ophthalmology*, Dec. 9, 2016, vol. 10, pp. 2455-2467.

Russian Office Action mailed Apr. 27, 2023 (including English language translation).

A. Papier et al., "Differential Diagnosis of the Swollen Red Eyelid," *Chinese Journal of Practical Rural Doctors*; 15(9):31-33 (2008).

A. Papier et al., "Differential Diagnosis of the Swollen Red Eyelid," *American Family Physician*, vol. 76, No. 12, Dec. 15, 2007, pp. 1816-1824.

C. Auw-Hädrich et al., "Behandlung der chronischen Blepharokeratokonjunktivitis mit lokalen Kalzineurininhibitoren" *Ophthalmologe* 2009, 106, pp. 635-638.

Elidel® FDA approved label 2014.

Viatris Press Release, "Update on Phase 3 Study of MR-139 for Blepharitis," PRNewswire Jul. 18, 2025.

ClinicalTrials.gov, NCT06400511, "A Phase 3 Study to Evaluate the Efficacy and Safety of Pimecrolimus 0.3% Ophthalmic Ointment," Jun. 6, 2025.

Moiseeva T.N. "Dry Eye Syndrome"// Dec. 26, 2018, Electronic source, URL: https://www.lotos74.ru/about/blog/sindromsukhogo-glaza/, paragraph 4.

A. B. Gottlieb et al., "Oral pimecrolimus in the treatment of moderate to severe chronic plaque-type psoriasis: a double-blind, multicentre, randomized, dose-finding trial," *Br. J. Dermatol.*, 2005, vol. 152, No. 6, pp. 1219-1227, PMID: 15948985.

* cited by examiner

Figure 1:

Structural formula of pimecrolimus

Figure 2

| Solvent | | Solubility % m/V [g/100 ml] | Description term[1] | X-ray analysis of the precipitate |
|---|---|---|---|---|
| Methanol | | 4.85 | s | Form B |
| Ethanol | | 2.63 | sps | Form B |
| Ethanol 95% | | 2.63 | sps | Form B |
| Ethanol/water 1:1 (V/V) | | 0.05 | vsls | Form B |
| Isopropyl alcohol | | 0.11 | sls | Form B |
| n-Heptane | | < 0.01 | ins | Form B |
| n-Hexane | | < 0.01 | ins | Form B |
| Acetonitrile | | 6.35 | s | Form B |
| Acetone | | > 25 | fs | Form B |
| t-Butyl methyl ether | | 1.37 | sps | Form B |
| n-Octanol | | 0.37 | sls | Form B |
| Propylene glycol | | 0.11 | sls | Form B |
| Hydrochloride acid 0.1 N | | < 0.01 | ins | Form B |
| buffer Glycin-HCl | pH 1.0 | < 0.01 | ins | Form B |
| buffer Citrate-HCl | pH 2.0 | < 0.01 | ins | Form B |
| buffer Citrate-HCl | pH 3.0 | < 0.01 | ins | Form B |
| buffer Phthalate | pH 4.0 | < 0.01 | ins | Form B |
| buffer Citrate-NaOH | pH 5.0 | < 0.01 | ins | Form B |
| buffer Citrate-NaOH | pH 6.0 | < 0.01 | ins | Form B |
| buffer Borate-HCl | pH 8.0 | < 0.01 | ins | Form B |
| Water | | < 0.01 | ins | Form B |

| Description term | | Approximate mass of solute [g] / volume of solvent [ml] | Solubility in percent [g/100 ml] approx. |
|---|---|---|---|
| vs | very soluble | > 1 g/ml | > 100% |
| fs | freely soluble | 1 g/ml – 1 g/10 ml | 10% - 100% |
| s | soluble | 1 g/10 ml – 1 g/30 ml | 3.3% - 10% |
| sps | sparingly soluble | 1 g/30 ml – 1 g/100 ml | 1% - 3.3% |
| sls | slightly soluble | 1 g/100 ml – 1 g/1000 ml | 0.1% - 1% |
| vsls | very slightly soluble | 1 g /1000 ml – 1 g/10'000 ml | 0.01% - 0.1% |
| ins | insoluble | < 1 g/10'000 ml | < 0.01% |

Figure 10

TREATMENT OF OCULAR DISEASE

BACKGROUND OF THE INVENTION

Blepharitis is a chronic inflammatory condition affecting the eyelids and eyelid margins, which may also subsequently impact the ocular surface. It is a form of dermatitis with involvement of skin, associated hairs, sebaceous glands, the muco-cutaneous junction and the meibomian glands.

Blepharitis often results in an unsightly redness & crusting of the eyelid margins, which disturbs patients. It is also uncomfortable with a broad spectrum of ocular symptoms ranging from mild transient irritation to persistent burning, itching, pain, contact lens intolerance, photophobia, ocular fatigue and visual disturbance. Symptoms are usually worse in the mornings and a patient may have multiple exacerbations.

In the most severe cases, ulceration and perforation of the cornea may occur. Though not normally sight-threatening, blepharitis is burdensome to both patients and the healthcare practitioners charged with their management.

Anterior and posterior blepharitis are common sub-classifications, based on the anatomic locations of the involved tissues. The aetiology and pathophysiology of blepharitis differ somewhat based on the type. Anterior blepharitis causes inflammation primarily at the base of the eyelashes. Posterior blepharitis affects the posterior lid margin (the section of the eyelid that comes into contact with the cornea and bulbar conjunctiva), and marginal blepharitis includes both anterior and posterior blepharitis. There is considerable overlap between these categories, which commonly co-exist and the treatments used today are largely the same.

Blepharitis and dry eye commonly co-exist and may present with similar symptomology, but they are recognised as distinct diseases, with a different pathogenesis and requiring specific treatment approaches. The Dry Eye Workshop (DEWS) committee, comprising the world's most eminent thought leaders in the field of ocular surface disease, published a report in 2017 [14], in which they presented their latest definition of dry eye, which clearly describes a pathology distinct from blepharitis;

"Dry eye is a multifactorial disease of the ocular surface characterised by a loss of homeostasis of the tear film, and accompanied by ocular symptoms, in which tear film instability and hyperosmolarity, ocular surface inflammation and damage, and neurosensory abnormalities play etiological roles."

Blepharitis is a very common disease. A survey of ophthalmologists and optometrists in the USA found that 37% and 47% respectively of their patients suffer from this disease [15] which is difficult to treat.

There are currently no approved pharmacological treatments for any of the forms of blepharitis in Europe or the US. In the absence of a recognised standard of care, 'off-label' topical antibiotics and topical steroids are the most widely prescribed treatments.

The are no randomised, controlled clinical trials to demonstrate topical antibiotics improve the signs and symptoms of blepharitis. A review of Lindsley et al. reports that for anterior blepharitis topical antibiotics provided some symptomatic relief and were effective in clearing bacteria from the eyelid margins [1]. However, it is unclear how the elimination of bacteria relates to clinical improvement for this condition. Indeed, the role of bacteria in the aetiology of the disease is poorly understood and the clinical evidence supporting an antibacterial treatment approach is underwhelming [2, 3]. Even in patients diagnosed with so-called staphylococcal blepharitis, only half of patients have positive cultures for *Staphylococcus aureus* [2].

Prolonged and/or excessive use of topical antibiotics is known to be a key driver of antimicrobial resistance (AMR) and there is evidence that the topical use of ocular antibiotics can induce bacterial resistance at extra ocular sites [10]. The threat posed to public health by the growing emergence of AMR is well publicised and has resulted in multiple antimicrobial stewardship programmes. In the absence of a clearly defined clinical benefit, the widespread use of prolonged courses of topical antibiotics to treat blepharitis contravenes the principles of prudent antimicrobial governance and may be contributing to the problem of increasing antimicrobial resistance.

Topical steroids may provide some symptomatic relief. Lid hygiene, including warm compresses and lid scrubs, showed some symptomatic relief in both anterior and posterior blepharitis. Overall, there was no strong evidence for any of the treatments in terms of effectively treating blepharitis.

Although the use of topical ocular steroids in such a chronic condition is a concern to many ophthalmologists, after topical antibiotics, this is the most commonly employed treatment modality. Only short courses are permissible, since prolonged dosing exposes patients to well-documented and sight-threatening side effects, namely, raised intra-ocular pressure, cataracts and opportunistic infections. Surprisingly, there is little published evidence to demonstrate the clinical benefit of topical steroids, even in the acute management of signs and symptoms, and they are contra-indicated for long-term treatment. However, it is very likely that some patients are being exposed to the risk of potentially serious side-effects, through inappropriately prolonged use of topical steroids, without compelling evidence of clinical benefit.

A novel treatment that meets the rigorous regulatory requirements for efficacy and safety would most likely become adopted as the accepted standard of care and in so doing, would decrease the potentially inappropriate use of topical antibiotics and topical steroids.

The active compound of the compositions and methods of this invention is pimecrolimus. Pimecrolimus is an immunomodulating agent of the calcineurin inhibitor class used in the treatment of atopic dermatitis (eczema). It is available as a topical cream, once marketed by Novartis under the trade name Elidel®. The preparation of pimecrolimus and pharmaceutical compositions containing pimecrolimus are disclosed in International Publications Nos. WO 01/60345 A2, WO 97/03654, WO 99/01458 and WO 01/90110 A1, U.S. Pat. Nos. 6,197,781 and 6,004,973 and in EP patents 1 754 482 A1, 1 482 936 B1 and 0 427 680 B1 all of which are hereby incorporated by reference in their entirety and for all purposes.

Pimecrolimus, an ascomycin macrolactam derivative, is a proven anti-inflammatory agent, which blocks transcription of "early" cytokines. The rationale for use of pimecrolimus in patients with blepharitis is to treat the disease by targeting the associated inflammation. Pimecrolimus has been shown to be highly potent in vitro and highly effective in animal models of skin inflammation [4]. In vivo data indicate that topical pimecrolimus has greater anti-inflammatory activity in the skin than cyclosporin A, but a lower potential for systemic immunosuppression than cyclosporin A and tacrolimus [5, 6, 7]. In contrast to steroids, pimecrolimus does not induce skin atrophy [4] and there is no evidence its ocular administration is associated with cataracts or raised intraocular pressure.

Topical ophthalmic compositions comprising an ascomycin have been proposed for use in the treatment of blepharitis (see for example EP1482936 and EP1754482). However, no clinical results are available that demonstrate the use of these ophthalmic compositions comprising an ascomycin in general, or pimecrolimus in particular, for the treatment of blepharitis.

For example, EP2319493 discloses various formulations that may comprise various active ingredients, amongst others, pimecrolimus. It is further disclosed that such formulations may be used in the treatment of blepharitis. However, no experimental or clinical data is shown in EP2319493 for the treatment of blepharitis with a formulation comprising pimecrolimus.

Auw-Hädrich and Reinhard reported that a clinical study with a 0.3% pimecrolimus ointment for the treatment of chronic blepharitis did not reveal significant differences in signs and symptoms compared to a placebo group [11]. However, no detailed information about the ingredients of the ointment, the design of the study and the analyzed signs and symptoms is available.

In a retrospective review of clinical cases, Kiiski et al. showed that a 1% pimecrolimus cream (Elidel®) for the treatment of atopic blepharoconjunctivitis was not well tolerated in the eye and elicited a poor clinical response [8]. Further, it was reported in another document that off-label use of a 1% pimecrolimus cream (Elidel®) for the treatment of blepharitis results in stinging eyes [9], mainly because Elidel® is not intended for ocular use and is poorly tolerated in the eye. It is a measure of the desperation of ophthalmologists that they are prepared to expose patients to the discomfort of these inappropriately formulated treatments.

Reports exist that pimecrolimus may be used for the treatment of dry eye disease. For example, Ousler et al. reported that an ophthalmic suspension comprising 0.3% pimecrolimus reduces corneal staining in dry eye patients [12]. Rynerson and Perry suggested that blepharitis and dry eye are not two distinct diseases and should instead be unified as dry eye blepharitis syndrome (DEBS) [13]. WO 2017/152027 (with Rynerson as the single inventor) discloses the use of biofilm inhibiting or disrupting compounds for the treatment of DEBS, however, the use of pimecrolimus is not disclosed in this document. Although blepharitis and dry eye may present with similar symptoms, that may even occur concomitantly in the same patient, they are two distinct diseases. Blepharitis is an inflammation of the eyelid and/or eyelid margin, whereas dry eye is defined as "a multifactorial disease of the ocular surface characterised by a loss of homeostasis of the tear film, and accompanied by ocular symptoms, in which tear film instability and hyperosmolarity, ocular surface inflammation and damage, and neurosensory abnormalities play etiological roles" [14]. Further, dry eye is currently treated by liquid formulations dropped directly into the eye.

Accordingly, there is a widely acknowledged need for providing an ophthalmic composition that shows a high patient acceptance and clinically meaningful improvement in the defined population of moderate to severe blepharitis patients.

SUMMARY OF THE INVENTION

The technical problem is solved by the embodiments provided herein and as characterised by the claims.

Accordingly, in one aspect, the invention relates to a composition comprising between 0.05% and 0.6% pimecrolimus, for use in the treatment of subjects with a clinical diagnosis of moderate to severe blepharitis.

That is, the present invention provides a pharmaceutical composition that is efficacious in the treatment of moderate to severe blepharitis. Example 7 shows that treatment of patients suffering from moderate to severe blepharitis characterised by swelling of the eyelid margin, ocular debris and ocular discomfort with a composition comprising 0.3% pimecrolimus results at least in reduced swelling of the eyelid margin and reduced ocular discomfort when compared to patients treated with a placebo/vehicle control without pimecrolimus. In contrast, it has been demonstrated that patients that do not fall strictly within the definition of moderate to severe blepharitis characterised by swelling of the eyelid margin, ocular debris and ocular discomfort, show no or only slight improvements in their signs and symptoms after treatment with the composition of the invention, when compared to patients treated with a placebo/vehicle control without pimecrolimus (Example 8). Thus, it was surprisingly found that a composition comprising 0.3% pimecrolimus is efficacious in the treatment of moderate to severe blepharitis, specifically characterised by swelling of the eyelid margin, ocular debris and ocular discomfort.

In previous studies, the main drawbacks when treating blepharitis with pimecrolimus have been the high levels of ocular intolerability, high discontinuation rates and poor efficacy. The efficacy and safety of pimecrolimus in the treatment of blepharitis was tested in a randomized, double-blind, placebo/vehicle-controlled proof-of-concept trial (CASM981 G2201) conducted by Novartis with the dermal 1% cream formulation (Elidel®). This study was terminated prematurely due to the ocular intolerability of the cream formulation when applied around the eyes. The conclusion from the clinical study report reads as follows; "The efficacy results of this final analysis confirm the interim results, which suggested that pimecrolimus cream 1% (dermatological formulation) when applied to the external eyelid will not prove to be efficacious for the treatment of blepharitis".

In a further study by Kiiski et al., 56% of all patients treated for atopic blepharoconjunctivitis with a 1% pimecrolimus cream (Elidel®) discontinued the treatment due to lack of treatment response or adverse events [8]. In contrast, within the present invention, only 20% of all patients that were treated with a composition according to the invention discontinued the treatment for the same reasons and a clear and clinically meaningful treatment effect was demonstrated.

Thus, it has been surprisingly found that treatment with the composition of the present invention comprising 0.3% pimecrolimus resulted in the improvement of signs and symptoms associated with moderate to severe blepharitis, and was well tolerated by patients compared to previous studies.

Bacteria are presumed to play a role in the aetiology of blepharitis and the majority of treatments prescribed to treat the condition contain an antibiotic. It is therefore surprising that a non-antibiotic treatment was able to show a consistent and sustained improvement in both the signs and symptoms of the disease compared to placebo/vehicle.

This is the first study ever to show a clinically meaningful improvement in both signs and symptoms in a randomised, double-blind, placebo/vehicle controlled clinical trial of moderate to severe blepharitis patients.

In Example 5, 67% of the patients treated with the composition according to the invention reported at least one adverse event, compared to 68% of the patients that were treated with a placebo/vehicle not containing any pimecrolimus (Table 5). The most common adverse event in this example was eye irritation, which was reported by 40% of the patients treated with the composition according to the invention and 32% of the patients treated with the placebo/vehicle (Table 6). In the patient groups of Example 6, 60% of the patients treated with the composition according to the invention reported at least one adverse event, compared to 55% of the patients that were treated with the placebo/vehicle and 29% of the patients treated with the composition according to the invention reported eye irritation compared to 24% of the patients treated with the placebo/vehicle (Tables 10 and 11). Accordingly, administration of pimecrolimus, when comprised in the composition according to the invention, does not result in a significant increase of adverse events compared to a placebo/vehicle control when applied to the human eyelid. Thus, the composition according to the invention surprisingly has an improved ocular tolerability compared to previous pimecrolimus-containing compositions when used for the treatment of blepharitis and is similar to vehicle/placebo.

Within the present invention, blepharitis is classified as mild or moderate to severe blepharitis. A subject is said to have moderate to severe blepharitis if all of the following signs and symptoms are fulfilled:

(i) A score of at least 2 (moderate) on swelling of the eyelid margin on a 0-4 scale, which corresponds to a diffuse swelling of the eyelid margin, a severe swelling of the eyelid margin with alterations in the eyelid folds, or a swelling which clearly reduces interpalpebral aperture (sign).

(ii) A score of at least 2 (moderate) on ocular debris on a 0-4 scale, which corresponds to a few fragments (6-20 collarettes), many fragments (21-40 collarettes), or clumps/strands (over 40 collarettes) on the eyelid margin (sign).

(iii) A symptom score of at least 40 mm (moderate) on ocular discomfort, which is assessed by the patient using a 100 mm visual analogue scale (symptom).

It is to be understood that a subject with a score of at least 2 for swelling of the eyelid margin and ocular debris and a symptom score of at least 40 mm for ocular discomfort is defined to have moderate to severe blepharitis. Thus, the term "moderate to severe blepharitis" is used interchangeably with "moderate to severe blepharitis characterised by swelling of the eyelid margin, ocular debris and ocular discomfort" in the context of this invention.

In particular, it is to be understood that no very severe form of blepharitis is defined within the present invention. That is, a subject with very severe signs (score 4) for swelling of the eyelid margin and ocular debris and a symptom score of at least 40 mm for ocular discomfort would still be classified within the present invention as having moderate to severe blepharitis.

Optionally, a subject that is diagnosed with moderate to severe blepharitis may also be suffering from redness of the eyelid margin. Swelling of the eyelid margin and redness of the eyelid margin frequently co-exist. Thus, in certain embodiments, a subject is determined to have moderate to severe blepharitis if the following signs and/or symptoms are fulfilled:

(i) a score of at least 2 on swelling of the eyelid margin AND redness of the eyelid margin on a 0-4 scale; and (ii) a score of at least 2 on ocular debris on a 0-4 scale; and (iii) a symptom score of at least 40 mm on ocular discomfort on a 100 mm visual analogue scale.

On the other hand, a subject is said to have no blepharitis or mild blepharitis, if the subject has a score lower than 2 for swelling of the eyelid margin and/or ocular debris and/or a symptom score lower than 40 mm for the ocular discomfort. In particular, it has been shown in Example 8 that subjects without ocular debris or only mild ocular debris do not benefit from a treatment with the composition of the invention. Thus, it is to be understood that subjects with none or mild ocular debris do not fall within the definition of moderate to severe blepharitis as used within the present invention.

Within, the present invention, it was surprisingly shown that the composition according to the invention is very efficacious in treating subjects with moderate to severe blepharitis characterised by swelling of the eyelid margin, ocular debris and ocular discomfort and, optionally, redness of the eyelid margin.

Accordingly, in one aspect, the invention relates to a composition comprising between 0.05% (wt/wt) and 0.6% (wt/wt) pimecrolimus, for use in the treatment of subjects with a clinical diagnosis of moderate to severe blepharitis, wherein the subjects to be treated have signs and symptoms of moderate to severe blepharitis characterised by swelling of the eyelid margin, ocular debris and ocular discomfort.

In a particular aspect, the invention relates to a composition comprising between 0.05% (wt/wt) and 0.6% (wt/wt) pimecrolimus, for use in the treatment of subjects with a clinical diagnosis of moderate to severe blepharitis, wherein a subject is determined to have moderate to severe blepharitis if the following signs and/or symptoms are fulfilled:

(i) a score of at least 2 on swelling of the eyelid margin on a 0-4 scale; and (ii) a score of at least 2 on ocular debris on a 0-4 scale; and (iii) a symptom score of at least 40 mm on ocular discomfort on a 100 mm visual analogue scale.

Thus, in certain embodiments, the invention relates to the composition for use according to the invention, wherein the subjects to be treated have:

(i) a score of at least 2 on swelling of the eyelid margin on a 0-4 scale; and (ii) a score of at least 2 on ocular debris on a 0-4 scale; and (iii) a symptom score of at least 40 mm on ocular discomfort on a 100 mm visual analogue scale.

In an alternative embodiment, the invention relates to a composition comprising between 0.05% (wt/wt) and 1% (wt/wt) pimecrolimus for use in the treatment of subjects with a clinical diagnosis of moderate to severe blepharitis, wherein the subjects to be treated have signs and symptoms of moderate to severe blepharitis characterised by swelling of the eyelid margin, ocular debris and ocular discomfort.

The skilled person is well aware of methods to determine the above-mentioned signs and symptoms without undue experimental burden and inventive skills. Example 4 further explains how to assess these signs and symptoms. To ensure unbiased and comparable assessment of signs of moderate to severe blepharitis, the severity of these signs may be interpreted from photographs.

It has been previously reported that an ointment comprising 0.3% pimecrolimus does not result in a significant improvement of signs and symptoms of chronic blepharitis compared to a placebo [11]. However, it has been shown that the composition of the present invention significantly improved several signs and symptoms related to moderate or severe blepharitis.

Accordingly, it has been surprisingly found within the present patent application that compositions comprising low concentrations of pimecrolimus, such as 0.3%, are efficacious in the treatment of subjects suffering from moderate to severe blepharitis, wherein the subjects to be treated have the following signs and symptoms:

(i) a score of at least 2 on swelling of the eyelid margin on a 0-4 scale; and
  (ii) a score of at least 2 on ocular debris on a 0-4 scale; and
  (iii) a symptom score of at least 40 mm on ocular discomfort on a 100 mm visual analogue scale.

That is, the present patent application identified a patient group which responds to the treatment with a composition comprising between 0.05% (wt/wt) and 0.6% (wt/wt) pimecrolimus, preferably between 0.1% (wt/wt) and 0.4% (wt/wt) pimecrolimus, more preferably 0.3% (wt/wt) pimecrolimus. In other embodiments, the patient group of the present patent invention may be treated with a composition comprising between 0.05% (wt/wt) and 1% (wt/wt) pimecrolimus.

Within the present invention, it is preferred that the composition according to the invention is administered to the affected area of a subject suffering from moderate to severe blepharitis. Accordingly, the composition according to the invention is preferably administered to the eyelid and/or the eyelid margin of said subject. During the administration of the composition according to the invention to the affected area or the eyelid of a subject suffering from moderate to severe blepharitis, it may occur that a portion of said composition may come into contact with the ocular surface tissue of the eye, such as cornea, conjunctiva and the like. Therefore, ocular compatibility of the composition according to the invention is a preferred aspect. According to the Examples of the present application, ocular compatibility of the composition according to the invention is surprisingly higher compared to other semi-solid pimecrolimus compositions known in the art.

The ingredients of a pharmaceutical composition are critical for its mode of administration. A preferred mode of administration of the composition according to the invention is topical administration. Corresponding compositions are in general administered topically to the skin, preferably to the skin around the eye lid, and in particular to the eye lid, preferably to the skin of the eye lid and/or the eyelid margin.

The term "composition", as used herein, refers to a composition comprising at least one pharmaceutically active ingredient and one or more pharmaceutically acceptable excipients. Herein, the pharmaceutically active ingredient, which is pimecrolimus, provides the therapeutic effect for the treatment of a disease in a subject or a group of subjects.

As used herein, "treatment" (and grammatical variations thereof such as "treat" or "treating") refers to clinical intervention in an attempt to alter the natural course of the subject being treated, and can be performed either for prophylaxis or for treatment of the signs and symptoms of moderate to severe blepharitis. Desirable effects of treatment include, but are not limited to, preventing occurrence or recurrence of disease, alleviation of signs and symptoms, diminishment of any direct or indirect pathological consequences of the disease, decreasing the rate of disease progression, amelioration or palliation of the disease state, and remission or improved prognosis. Within the present invention, the composition is preferably used for the treatment of moderate to severe blepharitis as defined above.

The term "subject" or the plural form "subjects" as used herein denote any animal, preferably a mammal, and more preferably a human. Examples of subjects include humans, non-human primates, rodents, guinea pigs, rabbits, sheep, pigs, goats, cattle, cows, horses, dogs and cats. Within the present invention, the terms "subject" and "patient" are used interchangeably. It is to be understood that the composition for use according to the invention or the method according to the invention may be used for the treatment of a single subject suffering from moderate to severe blepharitis, as well as for the treatment of groups of subjects suffering from moderate to severe blepharitis.

The term "clinical diagnosis" means a diagnosis that is based on knowledge obtained through medical history and physical examination alone or in conjunction with testing that provides supportive data for the diagnosis. Within the present invention, the clinical diagnosis may be based on signs and symptoms that are commonly associated with moderate to severe blepharitis.

Within the present invention, the composition for use in the treatment of subjects with a clinical diagnosis of moderate to severe blepharitis comprises pimecrolimus in an amount between 0.05 and 0.6% by weight (wt/wt). In a preferred embodiment the invention relates to a composition for use according to the invention comprising between 0.1% and 0.4% (wt/wt) pimecrolimus. In a more preferred embodiment, the invention relates to a composition for use according to the invention comprising 0.3% (wt/wt) pimecrolimus. In a particular embodiment, the invention relates to a composition for use according to the invention comprising 0.1% (wt/wt) pimecrolimus. In an alternative embodiment, the composition for use in the treatment of subjects with a clinical diagnosis of moderate to severe blepharitis comprises pimecrolimus in an amount between 0.05 and 1% by weight (wt/wt).

In one embodiment, the invention relates to a composition for use of according to the invention further comprising a medium-chain triglyceride and a microcrystalline wax.

That is, the composition for use according to the invention may comprise any combination of a medium-chain triglyceride and a microcrystalline wax in any amount.

The term "triglyceride" as used herein refers to an ester derived from glycerol and three fatty acids. Medium-chain triglycerides are triglycerides comprising C6 to C12 fatty acids, e.g. as known and commercially available under the trade name Acomed®, Myritol®, Captex®, Neobee® M5F, Miglyol®810, Miglyol®812, Mazol®, Sefsol®860 and Sefsol®870. Such medium-chain triglycerides are usually obtained from the oil extracted from the hard, dried fraction of the endosperm of *Cocos nucifera* or from the dried endosperm of *Elaeis guineensis*. They consist of a mixture of triglycerides of saturated fatty acids. Mainly of caprylic acid and of capric acid, and contain not less than 95 percent of saturated fatty acids with 8 to 10 carbon atoms.

A microcrystalline wax is characterised by its fine crystalline structure in contrast to the larger crystalline structure of paraffin wax. Microcrystalline waxes contain long, branched hydrocarbon chains. Microcrystalline waxes are more flexible, less oily, have higher tensile strength, more adhesion, and higher melting points than paraffin wax and have excellent gelling properties. The composition of the present invention may comprise any microcrystalline wax known in the art. Preferably, the microcrystalline wax comprised in the composition according to the invention follows the US Pharmacopeia (USP 43-NF38) requirements.

The composition of the present invention may comprise any medium-chain triglyceride in any amount that is suitable to obtain the claimed technical effect. In a preferred embodiment, the invention relates to a composition for use according to the invention, wherein the content of the medium-chain triglyceride is between 30% (wt/wt) and 60% (wt/wt). In a more preferred embodiment, the invention relates to a composition for use according to the invention, wherein the content of the medium-chain triglyceride is 50% (wt/wt).

The composition of the present invention may comprise any microcrystalline wax in any amount that is suitable to obtain the claimed technical effect. In a preferred embodiment, the invention relates to a composition for use according to the invention, wherein the content of the microcrystalline wax is between 3% (wt/wt) and 10% (wt/wt). In a more preferred embodiment, the invention relates to a composition according to the invention, wherein the content of the microcrystalline wax is 6% (wt/wt).

In a particular embodiment, the invention relates to a composition for use according to the invention comprising 0.3% pimecrolimus, 50% medium-chain triglyceride and 6% microcrystalline wax.

In another embodiment, the invention relates to a composition for use according to the invention comprising 0.1% pimecrolimus, 50% medium-chain triglyceride and 6% microcrystalline wax.

In another embodiment, the invention relates to a composition for use according to the invention comprising 1% pimecrolimus, 50% medium-chain triglyceride and 6% microcrystalline wax.

The composition according to the invention may comprise any medium-chain triglyceride in the above-mentioned amounts, provided that it is suitable to obtain the claimed technical effect. Preferably, the composition according to the invention comprises medium-chain triglycerides comprising decanoglycerides and/or octanoglycerides. Accordingly, in a preferred embodiment, the invention relates to a composition for use according to the invention, wherein the medium-chain triglyceride comprises caprylic acid and/or capric acid.

That is, the medium-chain triglyceride comprised in the composition according to the invention may comprise one, two or three caprylic acid fatty acid moieties and/or one, two or three capric acid fatty acid moieties. The medium-chain triglyceride comprised in the composition according to the invention may further be a mixture of triglycerides, wherein at least 95% of the triglycerides comprise one, two or three caprylic acid fatty acid moieties and/or one, two or three capric acid fatty acid moieties, respectively.

Caprylic acid is the common name for the eight-carbon saturated fatty acid known by the systematic name octanoic acid. Capric acid is a saturated medium-chain fatty acid with a ten-carbon backbone.

The commercially available medium-chain triglyceride Miglyol® 812 comprises caprylic acid and capric acid. Thus, in a more preferred embodiment, the invention relates to a composition for use according to the invention, wherein the medium-chain triglyceride is Miglyol® 812. In a particular embodiment, the invention relates to a composition for use according to the invention, wherein the medium chain triglyceride comprises a mixture of triglycerides with 50-64% C8 & 30-45% C10 saturated fatty acids.

The composition according to the present invention may be used for the treatment of subjects that show signs and symptoms of moderate to severe blepharitis. Accordingly, in another embodiment, the invention relates to a composition for use according to the invention in a patient population comprising subjects with signs and symptoms of moderate to severe blepharitis, wherein the subjects to be treated are characterised by swelling of the eyelid margin, ocular debris and ocular discomfort.

In a particular embodiment, the invention relates to a composition for use according to the invention, wherein the subjects to be treated have;
(i) a score of at least 2 (moderate) on swelling of the eyelid margin on a 0-4 scale

(ii) a score of at least 2 (moderate) on ocular debris on a 0-4 scale
(iii) a symptom score of at least 40 mm (moderate) on ocular discomfort on a 100 mm visual analogue scale.

That is, a subject is said to have moderate to severe blepharitis if all of the following signs and symptoms are fulfilled:
(i) A score of at least 2 (moderate) on swelling of the eyelid margin on a 0-4 scale, which corresponds to a diffuse swelling of the eyelid margin, a severe swelling of the eyelid margin with alterations in the eyelid folds, or a swelling which clearly reduces interpalpebral aperture (sign).
(ii) A score of at least 2 (moderate) on ocular debris on a 0-4 scale, which corresponds to a few fragments (6-20 collarettes), many fragments (21-40 collarettes), or clumps/strands (over 40 collarettes) on the eyelid margin (signs).
(iii) A symptom score of at least 40 mm (moderate) on ocular discomfort, which is assessed by the patient using a 100 mm visual analogue scale (symptom).

The skilled person is well aware of methods to determine the severity of the above-mentioned signs and symptoms without undue experimental burden and inventive skills. Example 4 further explains how to assess these signs and symptoms. To ensure unbiased and comparable assessment of signs of moderate to severe blepharitis, the severity of these signs may be interpreted from photographs.

In another embodiment, the invention relates to a composition for use in the treatment of moderate to severe blepharitis comprising 0.3% pimecrolimus, 50% medium-chain triglyceride and 6% microcrystalline wax, in a patient population comprising subjects with signs and symptoms of moderate to severe blepharitis, wherein the subjects to be treated are characterised by swelling of the eyelid margin, ocular debris and ocular discomfort.

In a particular embodiment, the invention relates to a composition for use in the treatment of moderate to severe blepharitis comprising 0.3% pimecrolimus, 50% medium-chain triglyceride and 6% microcrystalline wax, in subjects having;
(i) a score of at least 2 (moderate) on swelling of the eyelid margin on a 0-4 scale
(ii) a score of at least 2 (moderate) on ocular debris on a 0-4 scale
(iii) a symptom score of at least 40 mm (moderate) on ocular discomfort using a 100 mm visual analogue scale.

In another embodiment, the invention relates to a composition for use in the treatment of moderate to severe blepharitis comprising 0.1% pimecrolimus, 50% medium-chain triglyceride and 6% microcrystalline wax, in a patient population comprising subjects with signs and symptoms of moderate to severe blepharitis, wherein the subjects to be treated are characterised by swelling of the eyelid margin, ocular debris and ocular discomfort.

In a particular embodiment, the invention relates to a composition for use in the treatment of moderate to severe blepharitis comprising 0.1% pimecrolimus, 50% medium-chain triglyceride and 6% microcrystalline wax, in subjects having;
(i) a score of at least 2 (moderate) on swelling of the eyelid margin on a 0-4 scale
(ii) a score of at least 2 (moderate) on ocular debris on a 0-4 scale (iii) a symptom score of at least 40 mm (moderate) on ocular discomfort using a 100 nm visual analogue scale.

The term "patient population" as used herein refers to a subset of individuals that have been determined to show the signs and symptoms of moderate to severe blepharitis that are laid out above.

Example 7 includes subjects that have been diagnosed with moderate to severe blepharitis characterised by swelling of the eyelid margin, ocular debris and ocular discomfort for at least three months. Accordingly, in another embodiment, the invention relates to a composition for use according to the invention, wherein the subjects have been diagnosed with moderate to severe blepharitis characterised by swelling of the eyelid margin, ocular debris and ocular discomfort for at least three months. That is, the subject has received a diagnosis of moderate to severe blepharitis characterised by swelling of the eyelid margin, ocular debris and ocular discomfort three months ago or earlier.

In another embodiment, the invention relates to a composition for use according to the invention further comprising a preservative.

A preservative is a substance or a chemical that is added to products such as food, beverages, pharmaceutical drugs, paints, biological samples, cosmetics, wood, and many other products to prevent decomposition by microbial growth or by undesirable chemical changes.

The composition of the present invention may further comprise any preservative in any amount, provided that the composition retains its claimed technical effect in the presence of the preservative. The amount of the preservative in the composition according to the invention depends mainly on the type and the mode of action of the preservative. In a preferred embodiment, the invention relates to a composition for use according to the invention, wherein the content of the preservative is between 0.5% (wt/wt) and 2% (wt/wt). In a more preferred embodiment, the invention relates to a composition for use according to the invention, wherein the content of the preservative is 1.0%.

The preservative may be any preservative, preferably an ophthalmically acceptable preservative. Suitable preservatives include (a) a quaternary ammonium compound such as e.g. benzalkonium chloride (N-benzyl-N—(C8-C18-alkyl)-N, N-dimethylammonium chloride), benzoxonium chloride, benzethonium chloride, cetrimide (hexadecyltrimethylammonium bromide), sepazonium chloride, cetylpyridinium chloride, domiphen bromide (Bradosol®) or the like, (b) alkyl-mercury salts of thiosalicylic acid, such as e.g. thiomersal, phenylmercuric nitrate, phenylmercuric acetate or phenylmercuric borate, (c) parabens, such as e.g. methylparaben or propylparaben, (d) alcohols, such as e.g. chlorobutanol, benzyl alcohol or phenyl ethyl alcohol, (e) biguanide derivatives, such as e.g. chlorohexidine or polyhexamethylene biguanide, (f) sodium perborate, (g) imidazolidinyl urea as known and commercially available under the trade name Germal® II, (h) sorbic acid, (i) stabilized oxychloro complexes such as known and commercially available under the trade name Purite®, (k) polyglycol-polyamine condensation resins, such as known and commercially available e.g. under the trade name Polyquart® from Henkel KGaA, (l) stabilized hydrogen peroxide generated from a source of hydrogen peroxide for providing an effective trace amount of resultant hydrogen peroxide, e.g. sodium perborate tetrahydrate, and/or (m) a mixture of any components (a) to (l).

Preferably, the preservative comprised in the composition according to the invention is phenyl ethyl alcohol. Thus, in a preferred embodiment, the invention relates to a composition according to the invention, wherein the preservative is phenyl ethyl alcohol.

Phenyl ethyl alcohol, also known as phenethyl alcohol, 2-phenyl-ethan-1-ol or 2-phenyl ethanol, is an organic compound that consists of a phenethyl ($C_6H_5CH_2CH_2$) group attached to OH. It is a colourless liquid that is slightly soluble in water (2 ml/100 ml $H_2O$), but miscible with most organic solvents.

FIGS. 7 and 8 show that an improvement of eye swelling and ocular discomfort in patients with moderate to severe blepharitis that have been treated with the composition according to the invention was already observed two weeks after the start of the treatment. Accordingly, in certain embodiments, the invention relates to a composition for use according to the invention, wherein the treatment period is at least two weeks.

The positive effects of the treatment with the composition according to the invention on the signs and symptoms associated with moderate to severe blepharitis persist for six and twelve weeks of treatment. Thus, in another embodiment, the invention relates to a composition for use according to the invention, wherein the treatment period is between 6 weeks and 12 weeks, preferably wherein the treatment period is 6 or 12 weeks.

Tables 3, 4, 8 and 9 summarize the effects of the compositions according to the invention on signs and symptoms related to moderate to severe blepharitis after treatment for 12 weeks. Accordingly, in a preferred embodiment, the invention relates to a composition for use according to the invention, wherein the treatment period is 12 weeks.

In a particular embodiment, the invention relates to a composition for use according to the invention, wherein the treatment period is 6 weeks.

"Treatment period," as used herein means the length of time and/or frequency that a composition is applied to a target surface, in particular the eyelid and/or eyelid margin.

In another embodiment, the invention relates to a composition for use according to the invention, wherein at the end of the treatment the subjects show a clinically meaningful difference in the mean score improvement from baseline in at least one sign and/or symptom, in particular in at least one sign and one symptom.

That is, the treatment of a patient suffering from moderate to severe blepharitis with the composition according to the invention may result in an improvement of any sign or symptom related to moderate to severe blepharitis. Preferred signs and symptoms for the assessment of moderate to severe blepharitis are: ocular debris, pouting of the meibomian glands, redness of the eyelid margin, swelling of the eyelid margin and ocular discomfort.

A symptom is a departure from normal function or feeling which is apparent to a subject, reflecting the presence of an unusual state, or of a disease. A sign has the potential to be objectively observed by someone other than the subject, whereas a symptom does not. There is a correlation between this difference and the difference between the medical history and the physical examination. Some signs belong only to the physical examination, because it takes medical expertise to uncover them.

Within the present invention, the severity of signs of moderate to severe blepharitis may be quantified in score units ranging from 0 (no sign) to 4 (very severe sign). The severity of a symptom of moderate to severe blepharitis may be quantified in the form of an ocular discomfort score on a visual analogue scale ranging from 0 mm (no symptom) to 100 mm (severe symptom).

Ocular debris is a sign that is defined as the formation of discharge in the eye and may be quantified by counting the number of collarettes, which are crusting scales around the bases of eyelashes. The severity of ocular debris may be determined based on the number of collarettes per eye. To ensure unbiased and comparable results, the severity of ocular debris may be interpreted from photographs.

Pouting of meibomian glands is a sign that is described as an elevated internal plug of solidified secretions, which may be expressed from the orifice of a meibomian gland with pressure. The severity of pouting of meibomian glands may be quantified by determining the fraction of meibomian gland orifices that contain turbid or oily secretions. To ensure unbiased and comparable results, the severity of pouting of meibomian glands may be interpreted from photographs.

Redness of the eyelid margin is a sign that is defined as a painless or painful reddening of the eyelid margin. To ensure unbiased and comparable results, the severity of redness of the eyelid margin may be interpreted from photographs.

Swelling of the eyelid margin is a sign that is defined as a painless or painful abnormal protuberance or enlargement of the eyelid margin. To ensure unbiased and comparable results, the severity of swelling of the eyelid margin may be interpreted from photographs.

It is to be understood that swelling of the eyelid margin is often accompanied by redness of the eyelid margin. Thus, a subject suffering from moderate to severe blepharitis characterised by swelling of the eyelid margin, ocular debris and ocular discomfort is frequently diagnosed with redness of the eyelid margin as well.

Ocular discomfort is a generic expression that describes a lack of ease in/about the eyes. Since ocular discomfort can only be perceived by a subject suffering from ocular discomfort, it is classified as a symptom. Accordingly, the severity of ocular discomfort has to be determined by said subject. Subjects suffering from ocular discomfort may describe at least one of the following symptoms: eyelid itching, foreign body sensation/grittiness, ocular dryness, ocular burning/pain, heavy eyelids, sensitivity to light and/or blurred vision. To quantify the severity of ocular discomfort, a visual analogue scale may be used.

Scores may be specified as mean scores for a population of subjects. A mean score for a specific sign may be calculated by adding the scores for this sign of all subjects in the population and by dividing the sum of these scores by the number of subjects in the population. A mean score for ocular discomfort (symptom) may be calculated by adding the ocular discomfort scores for all subjects in the population and by dividing the sum of these ocular discomfort scores by the number of subjects in the population.

The baseline is defined as the score that has been determined at the beginning of the treatment. The baseline may be a score that has been determined for a single subject at the beginning of the treatment or may be a mean score that has been determined for a population of subjects at the beginning of the treatment. Preferably, the baseline is expressed as a mean score for a population. A score or mean score is said to be improved from baseline, if the score or mean score at the end of a treatment is lower compared to the score or mean score for the same sign or for ocular discomfort at the beginning of the treatment.

Within the present invention, a difference in a sign is said to be clinically meaningful, if the score or mean score measured at the end of the treatment is at least 1 score unit lower than the score or mean score measured at the beginning of the treatment (baseline). A difference in ocular discomfort (symptom) is said to be clinically meaningful, if the ocular discomfort score or mean ocular discomfort score measured at the end of the treatment is at least 30 mm lower than the ocular discomfort score or mean ocular discomfort score measured at the beginning of the treatment (baseline).

Accordingly, in a preferred embodiment, the invention relates to a composition for use according to the invention, wherein at the end of the treatment the subjects show at least a 1 score unit mean improvement from baseline for swelling of the eyelid margin and/or ocular debris (sign) and at least a 30 mm mean improvement from baseline for ocular discomfort (symptom)

Within the present invention, the severity of swelling of the eyelid margin is illustrated as a score ranging from 0 (no swelling) to 4 (very severe swelling). FIGS. 3, 5 and 7, as well as Tables 3 and 8 show that the treatment of subjects with the composition according to the invention reduced the mean score in patients at least by 1 score unit from baseline, which is considered to be clinically meaningful. Accordingly, in another embodiment, the invention relates to a composition according to the invention, wherein at the end of the treatment the subject or subjects show(s) at least a 1 score unit reduction in the score or mean score compared to the baseline for swelling of the eyelid margin.

The severity of ocular discomfort is illustrated on a visual analogue scale ranging from 0 mm (no ocular discomfort) to 100 mm (severe ocular discomfort). FIGS. 4, 6, and 8, as well as Tables 4 and 9 show that the treatment of subjects with the composition according to the invention resulted in an at least 30 mm reduction from the baseline in the mean ocular discomfort score (on the visual analogue scale) by the end of the treatment. Thus, within the present invention, a subject is determined to show a clinically meaningful improvement for ocular discomfort, if the subject shows at least a 30 mm reduction from the baseline on a visual analogue scale ranging from 0 mm to 100 mm at the end of the treatment.

Alternatively and preferably, a mean score is defined to be improved from baseline compared to the placebo/vehicle, if the mean score improvement from baseline for a sign or symptom at the end of a treatment with the composition according to the invention is greater than the mean score improvement from baseline with a placebo/vehicle.

Thus, in an alternative embodiment, the invention relates to a composition for use according to the invention, wherein at the end of the treatment the subjects show a clinically meaningful difference in the mean score improvement from baseline compared to the placebo/vehicle in at least one sign and/or symptom, in particular in at least one sign and one symptom.

In a preferred embodiment, the invention relates to a composition for use according to the invention, wherein at the end of the treatment the subjects show a greater mean score improvement from baseline compared to the placebo/vehicle in at least one sign and/or symptom, in particular in at least one sign and one symptom, wherein the treatment period is between 6 and 12 weeks.

In a more preferred embodiment, the invention relates to a composition for use according to the invention, wherein at the end of the treatment the subjects show a greater mean score improvement from baseline compared to the placebo/vehicle in at least one sign and/or symptom, in particular in at least one sign and one symptom, wherein the treatment period is 6 or 12 weeks.

In an even more preferred embodiment, the invention relates to a composition for use according to the invention, wherein at the end of the treatment the subjects show a greater mean score improvement from baseline compared to the placebo/vehicle in at least one sign and/or symptom, in particular in at least one sign and one symptom, wherein the treatment period is between 6 and 12 weeks and wherein the composition is administered to the eyelid and/or the eyelid margin once, twice, three times or four times daily.

In an even more preferred embodiment, the invention relates to a composition for use according to the invention, wherein at the end of the treatment the subjects show a greater mean score improvement from baseline compared to the placebo/vehicle in at least one sign and/or symptom, in particular in at least one sign and one symptom, wherein the treatment period is 6 or 12 weeks and wherein the composition is administered to the eyelid and/or the eyelid margin once, twice, three times or four times daily.

In a most preferred embodiment, the invention relates to a composition for use according to the invention, wherein at the end of the treatment the subjects show a greater mean score improvement from baseline compared to the placebo/vehicle in at least one sign and/or symptom, in particular in at least one sign and one symptom, wherein the treatment period is 6 or 12 weeks and wherein the composition is administered to the eyelid and/or the eyelid margin twice daily.

In a particular embodiment, the invention relates to a composition for use according to the invention, wherein at the end of the treatment the subjects show a greater mean score improvement from baseline compared to the placebo/vehicle in at least one sign and/or symptom, in particular in at least one sign and one symptom, wherein the treatment period is 2 weeks and wherein the composition is administered to the eyelid and/or the eyelid margin twice daily.

In certain embodiments, the invention relates to a composition for use according to the invention, wherein at the end of the treatment the subjects show a greater mean score improvement from baseline (compared to a placebo/vehicle) in at least one sign and/or symptom, wherein the sign and/or symptom is at least one selected from a group consisting of: ocular debris, pouting of the meibomian glands, redness of the eyelid margin, swelling of the eyelid margin and ocular discomfort.

That is, in certain embodiments, the invention relates to a composition for use according to the invention, wherein at the end of the treatment the subjects show a greater mean score improvement from baseline (compared to a placebo/vehicle) in ocular debris, pouting of the meibomian glands, redness of the eyelid margin, swelling of the eyelid margin or ocular discomfort.

In a particular embodiment, the invention relates to a composition for use according to the invention, wherein at the end of the treatment the subjects show a greater mean score improvement from baseline (compared to a placebo/vehicle) in swelling of the eyelid margin and ocular debris.

In a particular embodiment, the invention relates to a composition for use according to the invention, wherein at the end of the treatment the subjects show a greater mean score improvement from baseline (compared to a placebo/vehicle) in swelling of the eyelid margin and ocular discomfort.

In a particular embodiment, the invention relates to a composition for use according to the invention, wherein at the end of the treatment the subjects show a greater mean score improvement from baseline (compared to a placebo/vehicle) in ocular discomfort and ocular debris.

In a particular embodiment, the invention relates to a composition for use according to the invention, wherein at the end of the treatment the subjects show a greater mean score improvement from baseline (compared to a placebo/vehicle) in swelling of the eyelid margin, ocular discomfort and ocular debris.

An improvement in a sign is said to be clinically meaningful, if the mean score improvement from baseline at the end of a treatment with the composition according to the invention is at least 0.2, preferably at least 0.3, 0.4, score units greater than the mean score improvement from baseline with a placebo/vehicle.

Tables 3 and 8 show that the treatment of subjects with the composition according to the invention reduced the mean score from baseline compared to the placebo/vehicle across patients by at least 0.2 score units at the end of the treatment. Thus, in one embodiment, the invention relates to a composition according to the invention, wherein at the end of the treatment subjects show at least a 0.05, 0.1, 0.15, 0.2, 0.3, 0.4 greater mean score unit improvement from baseline compared to the placebo/vehicle for swelling of the eyelid margin and/or ocular debris (signs).

An improvement in ocular discomfort is said to be clinically meaningful, if the mean ocular discomfort score improvement from baseline at the end of a treatment with the composition according to the invention is at least 10 mm greater than the mean ocular discomfort score improvement from baseline with a placebo/vehicle.

Tables 4 and 9 further show that the treatment of subjects with the composition according to the invention reduced the mean ocular discomfort score on the visual analogue scale compared to the placebo/vehicle by at least 10 mm at the end of the treatment. Thus, in another embodiment, the invention relates to a composition according to the invention, wherein at the end of the treatment subjects show at least a 1, 2, 3, 4, 5, 6, 7, 8, 9, preferably 10 mm greater reduction in the improvement from baseline compared to the placebo/vehicle for ocular discomfort (symptom).

Thus, the invention relates to a composition for use according to the invention, wherein at the end of the treatment subjects show at least a 0.2, preferably at least a 0.3, more preferably at least 0.4 score unit greater mean improvement from baseline compared to the placebo/vehicle for swelling of the eyelid margin and/or ocular debris (signs) and a mean score improvement from baseline compared to the placebo/vehicle for ocular discomfort (symptom).

Thus, the invention relates to a composition for use according to the invention, wherein at the end of the treatment subjects show at least a 0.2, preferably at least a 0.3, more preferably at least 0.4 score unit greater mean improvement from baseline compared to the placebo/vehicle for swelling of the eyelid margin and/or ocular debris (signs) and wherein the subjects show at least a 1, 2, 3, 4, 5, 6, 7, 8, 9, preferably 10 mm greater mean reduction in the improvement from baseline compared to the placebo/vehicle for ocular discomfort (symptom).

Within the present invention, a subject is said to have moderate to severe blepharitis, if the subject has a score of at least a score of 2 on swelling of the eyelid margin and ocular debris, as well as an ocular discomfort score of at least 40 m (symptom). Subjects falling under this definition were treated in Example 7.

The results for swelling of the eyelid margin at the end of a 6 weeks or 12 weeks treatment for subjects suffering from moderate to severe blepharitis (Baseline>=2) are shown in FIG. 7. Accordingly, for subjects suffering from moderate to severe blepharitis, the treatment with the composition according to the invention reduced the mean score from baseline by 0.6 score units more than the placebo/vehicle at the end of the 2 weeks treatment, by 0.7 score units more than the placebo/vehicle at the end of the 6 weeks treatment and by 0.4 score units more than the placebo/vehicle at the end of the 12 weeks treatment. Thus, in a more preferred embodiment, the invention relates to a composition according to the invention, wherein at the end of the treatment subjects show at least a 0.2, preferably at least a 0.3, more preferably at least a 0.4 score unit greater improvement from baseline compared to the placebo/vehicle for the mean score for swelling of the eyelid margin and/or the mean score for ocular debris (signs).

Thus, the invention relates to a composition for use according to the invention, wherein at the end of the treatment subjects show at least a 0.2, preferably at least a 0.3, more preferably at least a 0.4 score unit greater improvement from baseline compared to the placebo/vehicle for the mean score for swelling of the eyelid margin and/or the mean score for ocular debris (signs) and a greater improvement from baseline compared to the placebo/vehicle for the mean score for ocular discomfort (symptom).

The results for ocular discomfort at the end of a 6 weeks or 12 weeks treatment for subjects suffering from moderate to severe blepharitis (Baseline>=40 mm) are shown in FIG. 8. Accordingly, for subjects suffering from moderate to severe blepharitis, treatment with the composition according to the invention reduced the mean symptom score from baseline by 17 mm score units more than the placebo/vehicle at the end of the 2 weeks treatment, by 16 mm score units more than the placebo/vehicle at the end of the 6 weeks treatment and by 14 mm score units more than the placebo/vehicle at the end of the 12 weeks treatment. Thus, in a more preferred embodiment, the invention relates to a composition according to the invention, wherein at the end of the treatment subjects show at least a 1, 2, 3, 4, 5, 6, 7, 8, 9, preferably a 10 mm greater improvement from baseline compared to the placebo/vehicle for the mean score for ocular discomfort (symptom). In certain embodiments, the invention relates to a composition according to the invention, wherein at the end of the treatment subjects show at least a 12, 13 or 14 mm greater improvement from baseline compared to the placebo/vehicle for the mean score for ocular discomfort (symptom).

Thus, the invention relates to a composition for use according to the invention, wherein at the end of the treatment subjects show at least a 0.2, preferably at least a 0.3, more preferably at least a 0.4 score unit greater improvement from baseline compared to the placebo/vehicle for the mean score for swelling of the eyelid margin and/or the mean score for ocular debris (signs) and wherein subjects show at least a 1, 2, 3, 4, 5, 6, 7, 8, 9, preferably at least a 10 mm greater improvement from baseline compared to the placebo/vehicle for the mean score for ocular discomfort (symptom).

Thus, in certain embodiments, the invention relates to a composition for use according to the invention, wherein at the end of the treatment the subjects show at least a 0.4 score unit greater improvement from baseline compared to a placebo/vehicle for the mean score for swelling of the eyelid margin and/or the mean score for ocular debris (signs) and an improvement compared to the placebo/vehicle for the mean score for ocular discomfort (symptom).

In further embodiments, the invention relates to a composition for use according to the invention, wherein at the end of the treatment the subjects show at least a 0.4 score unit greater improvement from baseline compared to a placebo/vehicle for the mean score for swelling of the eyelid margin and/or the mean score for ocular debris (signs) and an at least 10 mm greater improvement, in particular an at least 12, 13, 14 mm greater improvement, compared to the placebo/vehicle for the mean score for ocular discomfort (symptom).

In a preferred embodiment, the invention relates to a composition for use according to the invention, wherein at the end of the treatment the subjects show at least a 0.4 score unit greater improvement from baseline compared to a placebo/vehicle for the mean score for swelling of the eyelid margin and/or the mean score for ocular debris (signs) and an improvement compared to the placebo/vehicle for the mean score for ocular discomfort (symptom), wherein the treatment period is between 6 and 12 weeks, or, alternatively, wherein the treatment period is 2 weeks.

In a more preferred embodiment, the invention relates to a composition for use according to the invention, wherein at the end of the treatment the subjects show at least a 0.4 score unit greater improvement from baseline compared to a placebo/vehicle for the mean score for swelling of the eyelid margin and/or the mean score for ocular debris (signs) and an improvement compared to the placebo/vehicle for the mean score for ocular discomfort (symptom), wherein the treatment period is 6 or 12 weeks, or, alternatively, wherein the treatment period is 2 weeks.

In an even more preferred embodiment, the invention relates to a composition for use according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and an improvement compared to the placebo/vehicle for the mean score for ocular discomfort (symptom), wherein the treatment period is between 6 and 12 weeks, or, alternatively, wherein the treatment period is 2 weeks, and wherein the composition is administered to the eyelid and/or the eyelid margin once, twice, three times or four times daily.

In an even more preferred embodiment, the invention relates to a composition for use according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and an improvement compared to the placebo/vehicle for the mean score for ocular discomfort (symptom), wherein the treatment period is 6 or 12 weeks, or, alternatively, wherein the treatment period is 2 weeks, and wherein the composition is administered to the eyelid and/or the eyelid margin once, twice, three times or four times daily.

In a most preferred embodiment, the invention relates to a composition for use according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and an improvement compared to the placebo/vehicle for the mean symptom score for ocular discomfort (symptom), wherein the treatment period is 6 or 12 weeks and wherein the composition is administered to the eyelid and/or the eyelid margin twice daily.

In certain embodiments, the invention relates to a composition for use according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and an improvement compared to the placebo/vehicle for the mean symptom score for ocular discomfort (symptom), wherein the treatment period is 2 weeks and wherein the composition is administered to the eyelid and/or the eyelid margin twice daily.

In other embodiments, the invention relates to a composition for use according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and an at least 10 mm greater improvement, in particular an at least 12, 13, 14 mm greater improvement, compared to the placebo/vehicle for the mean symptom score for ocular discomfort (symptom), wherein the treatment period is 2 weeks and wherein the composition is administered to the eyelid and/or the eyelid margin twice daily.

In a particular embodiment, the invention relates to a composition for use according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and at least a 10 mm greater improvement from baseline, in particular at least a 12, 13, 14 mm greater improvement from baseline, compared to the placebo/vehicle for the mean score for ocular discomfort (symptom), in particular wherein the treatment period is 6 or 12 weeks and wherein the composition is administered to the eyelid and/or the eyelid margin twice daily.

The term "placebo/vehicle" as used herein refers to a composition that is identical to the composition according to the invention, with the exception that it does not contain the active ingredient of the composition, in this case pimecrolimus. In another embodiment, the invention relates to a composition for use according to the invention, which is formulated as an ointment.

The composition according to the invention may be formulated in any way, provided that the composition retains its claimed technical effect. Preferably, the composition according to the invention may be formulated as an ointment. Suitable ointment bases include for example ophthalmically acceptable oil and fat bases. Suitable ointment bases are (a) natural wax e.g. white and yellow bees wax, carnauba wax, wool wax (wool fat), purified lanolin, anhydrous lanolin,
(b) petroleum wax e.g. hard paraffin, microcrystalline wax,
(c) hydrocarbons e.g. liquid paraffin, white and yellow soft paraffin, white petrolatum, yellow petrolatum, or
(d) combinations thereof.

Within the present invention the ointment is preferably based on white petrolatum.

In certain embodiments, the composition of the invention is an ointment comprising 0.1% or 0.3% pimecrolimus, 50% medium-chain triglyceride, 6% microcrystalline wax and an ointment base, wherein the ointment base is preferably white petrolatum.

In other embodiments, the composition of the invention is an ointment comprising 0.1% or 0.3% pimecrolimus, 50% medium-chain triglyceride, 6% microcrystalline wax, 1% phenyl ethyl alcohol and an ointment base, wherein the ointment base is preferably white petrolatum.

In a further embodiment, the composition of the invention is an ointment consisting of 0.1% or 0.3% pimecrolimus, 50% medium-chain triglyceride, 6% microcrystalline wax and an ointment base, wherein the ointment base is preferably white petrolatum.

In a further embodiment, the composition of the invention is an ointment consisting of 0.1% or 0.3% pimecrolimus, 50% medium-chain triglyceride, 6% microcrystalline wax, 1% phenyl ethyl alcohol and an ointment base, wherein the ointment base is preferably white petrolatum.

It has to be noted that developing a stable formulation in an ointment base, that was well-tolerated in the eye, was technically challenging. Pimecrolimus is highly hydrophobic and highly insoluble (see FIG. 2). Solubility of pimecrolimus in excipients that can be used in semi-solid formulations for dermal, and particularly for ophthalmic use, is very poor and oversaturated solutions have to be avoided because of the risk of crystallization and/or bleeding when stress (e.g. thermal, shear) is applied. Thus, an inventive activity was required to arrive at a stable ointment according to the invention, wherein the pimecrolimus remains in solution and does not crystallize. In order to dissolve pimecrolimus, a large volume of liquid solvent (medium chain triglycerides) needs to be used and this makes it technically challenging to derive an appropriately viscous ointment that is suitable for topical application and adherence to the eyelid and eyelid margin.

The strong emollient effect of the ointment makes it useful in dry skin conditions and its occlusive effect enhances penetration of active drug and improves efficacy (especially in thickened, lichenified skin). The ointment provides a protective film on the skin and has greasy, sticky consistency that retains sweat. Usually, ointments contain little to no water. Example 2 describes a composition according to the invention that is formulated as a water-free white petrolatum-based ointment.

Besides the active ingredient pimecrolimus, the ointment according to the invention may comprise one or more excipients. Information on the properties, specifications and characteristics of the excipients are described e.g. in standard texts such as Fiedler, H. P.; 1996; Lexikon der Hilfsstoffe für Pharmazie, Kosmetik und angrenzende Gebiete; Editio Cantor Verlag Aulendorf (Germany), and Kibbe, A. H.; 2000; Handbook of Pharmaceutical Excipients, a joint publication of Pharmaceutical Press, London (UK), and American Pharmaceutical Association, Washington (US) as well as manufacturers' brochures. Preferably, all excipients in the composition of the invention, in particular the ointment of the invention, follow the US and/or European Pharmacopeia requirements.

In another embodiment, the invention relates to a composition for use according to the invention, wherein a unit dosage of the composition is administered once, twice, three times, four times a day.

That is, the composition according to the invention may be administered to the affected area, preferably the eyelid and/or the eyelid margin, once, twice, three times or four times a day. In a preferred embodiment, the invention relates to a method according to the invention, wherein a unit dosage of the composition is administered twice a day.

The term "unit dosage", as used herein, refers to a physically discrete unit suitable as unitary dosage for human and animal subjects. Each unit contains a predetermined quantity of the composition according to the invention calculated in an amount sufficient to produce the desired effect. The amount of the unit dosage of the composition according to the invention depends on various factors, such as the concentration of the active agent pimecrolimus in the composition, the effect to be achieved and the pharmaco-dynamics associated with the active agent in the subject. Preferably, a unit dosage is defined as an amount that is sufficient to cover the eyelid and/or the eyelid margin with a thin layer of the composition according to the invention. Alternatively, a unit dosage is defined as a 3 mm strip of the composition. The 3 mm strip may be applied to the eyelids up to and including the eyelid margin after routine morning and evening lid hygiene.

In another embodiment, the invention relates to a composition for use according to the invention, wherein the composition is applied to the eyelid, in particular to the eyelid margin, with an applicator.

The eye is a delicate organ and self-application of the composition according to the invention may prove difficult for some subjects. Accordingly, administration of the composition according to the invention to the eyelid or, in particular, the eyelid margin may be facilitated with an applicator. The applicator may be any applicator that is known in the art for the application of creams or ointments to skin, in particular the skin of the eyelid and/or the eyelid margin. Preferably the applicator may be of a soft or flexible material to prevent damage of eye tissue. Further, the applicator may comprise an antimicrobial material to prevent infection of the eye or the eyelid. The applicator may be for repeated use or single use.

In another embodiment, the invention relates to a composition for use according to the invention for use in human or veterinary therapy.

That is, the composition according to the invention may be used for the treatment of moderate to severe blepharitis in humans and/or animals.

In one aspect, the invention relates to an applicator comprising the composition according to the invention.

In another aspect, the invention relates to a method of treating subjects with a clinical diagnosis of moderate to severe blepharitis, the method comprising administering to said subjects a composition comprising between 0.05% and 0.6% pimecrolimus. Preferably, the method of the invention comprises administration of a composition comprising between 0.1% and 0.4% pimecrolimus. Alternatively, the invention relates to a method of treating subjects with a clinical diagnosis of moderate to severe blepharitis, the method comprising administering to said subjects a composition comprising between 0.05% and 1% pimecrolimus.

In another embodiment, the invention relates to a method according to the invention, wherein the subjects to be treated show signs and symptoms of moderate to severe blepharitis characterised by swelling of the eyelid margin, ocular debris and ocular discomfort. In a particular embodiment, the invention relates to a method according to the invention, wherein the subjects to be treated show all of the following signs and/or symptoms:

(i) a score of at least 2 (moderate) on swelling of the eyelid margin on a 0-4 scale; and/or (ii) a score of at least 2 (moderate) on ocular debris on a 0-4 scale; and/or (iii) a symptom score of at least 40 mm (moderate) for ocular discomfort on a 100 mm visual analogue scale.

In one embodiment, the invention relates to a method according to the invention, wherein the composition is a composition as defined according to the invention.

In one embodiment, the invention relates to a method according to the invention, wherein the composition comprises 0.3% pimecrolimus, 50% medium-chain triglyceride, 6% microcrystalline wax and 1% preservative.

In a particular embodiment, the invention relates to a method according to the invention, wherein the composition comprises 0.1% pimecrolimus, 50% medium-chain triglyceride, 6% microcrystalline wax and 1% preservative.

In certain embodiments, the invention relates to a method according to the invention, wherein the composition is an ointment, in particular wherein the ointment is based on white petrolatum.

In certain embodiments, the invention relates to a method according to the invention, wherein the composition is an ointment comprising or consisting of: 0.1% or 0.3% pimecrolimus, 50% medium-chain triglyceride, 6% microcrystalline wax and white petrolatum.

In certain embodiments, the invention relates to a method according to the invention, wherein the composition is an ointment comprising or consisting of: 0.1% or 0.3% pimecrolimus, 50% medium-chain triglyceride, 6% microcrystalline wax, 1% phenyl ethyl alcohol and white petrolatum.

In one embodiment, the invention relates to a method according to the invention, wherein a single unit dosage of the composition is administered once, twice, three times, four times a day.

In one aspect, the invention relates to a method for the treatment of moderate to severe blepharitis comprising administering twice a day a composition comprising 0.3% pimecrolimus, 50% medium-chain triglyceride, 6% microcrystalline wax and 1% preservative, to a patient population comprising subjects with signs and symptoms of moderate to severe blepharitis characterised by swelling of the eyelid margin, ocular debris and ocular discomfort.

In a particular embodiment, the invention relates to a method for the treatment of moderate to severe blepharitis comprising administering twice a day a composition comprising 0.3% pimecrolimus, 50% medium-chain triglyceride, 6% microcrystalline wax and 1% preservative, in subjects having;

(i) a score of at least 2 (moderate) on swelling of the eyelid margin on a 0-4 scale;

(ii) a score of at least 2 (moderate) on ocular debris on a 0-4 scale; and (iii) a symptom score of at least 40 mm (moderate) on ocular discomfort on a 100 mm visual analogue scale.

In another aspect, the invention relates to a method for the treatment of moderate to severe blepharitis comprising administering twice a day a composition comprising 0.1% pimecrolimus, 50% medium-chain triglyceride, 6% microcrystalline wax and 1% preservative, to a patient population comprising subjects with signs and symptoms of moderate to severe blepharitis characterised by swelling of the eyelid margin, ocular debris and ocular discomfort.

In a particular embodiment, the invention relates to a method for the treatment of moderate to severe blepharitis comprising administering twice a day a composition comprising 1% pimecrolimus, 50% medium-chain triglyceride, 6% microcrystalline wax and 1% preservative, to a patient population comprising subjects having;

(i) a score of at least 2 (moderate) on swelling of the eyelid margin on a 0-4 scale;

(ii) a score of at least 2 (moderate) on ocular debris on a 0-4 scale; and (iii) a symptom score of at least 40 mm (moderate) on ocular discomfort on a 100 mm visual analogue scale.

In one embodiment, the invention relates to a method according to the invention, wherein the treatment period is between 6 weeks and 12 weeks.

In a preferred embodiment, the invention relates to a method according to the invention, wherein the treatment period is 6 weeks.

In a particular embodiment, the invention relates to a method according to the invention, wherein the treatment period is 12 weeks.

In a particular embodiment, the invention relates to a method according to the invention wherein the treatment period is at least 2 weeks.

In one embodiment, the invention relates to a method according to the invention, wherein at the end of the treatment the subjects show a clinically meaningful difference in the mean score improvement from baseline compared to a placebo/vehicle in at least one sign and/or symptom, in particular in at least one sign and one symptom.

In certain embodiments, the invention relates to a method according to the invention, wherein at the end of the treatment the subjects show a greater mean score improvement from baseline compared to a placebo/vehicle in at least one sign and/or symptom, in particular in at least one sign and one symptom, wherein the treatment period is between 6 and 12 weeks, or, alternatively, wherein the treatment period is 2 weeks.

In certain embodiments, the invention relates to a method according to the invention, wherein at the end of the treatment the subjects show a greater mean score improvement from baseline compared to the placebo/vehicle in at least one sign and/or symptom, in particular in at least one sign and one symptom, wherein the treatment period is 6 or 12 weeks, or, alternatively, wherein the treatment period is 2 weeks.

In certain embodiments, the invention relates to a method according to the invention, wherein at the end of the treatment the subjects show a greater mean score improvement from baseline compared to the placebo/vehicle in at least one sign and/or symptom, in particular in at least one sign and one symptom, wherein the treatment period is between 6 and 12 weeks, or, alternatively, wherein the treatment period is 2 weeks, and wherein the composition is administered to the eyelid and/or the eyelid margin once, twice, three times or four times daily.

In certain embodiments, the invention relates to a method according to the invention, wherein at the end of the treatment the subjects show a greater mean score improvement from baseline compared to the placebo/vehicle in at least one sign and/or symptom, in particular in at least one sign and one symptom, wherein the treatment period is 6 or 12 weeks, or, alternatively, wherein the treatment period is 2 weeks, and wherein the composition is administered to the eyelid and/or the eyelid margin once, twice, three times or four times daily.

In certain embodiments, the invention relates to a method according to the invention, wherein at the end of the treatment the subjects show a greater mean score improvement from baseline compared to the placebo/vehicle in at least one sign and/or symptom, in particular in at least one sign and one symptom, wherein the treatment period is 6 or 12 weeks, or, alternatively, wherein the treatment period is 2 weeks, and wherein the composition is administered to the eyelid and/or the eyelid margin twice daily.

In certain embodiments, the invention relates to a method according to the invention, wherein at the end of the treatment the subjects show a greater mean score improvement from baseline compared to a placebo/vehicle in at least one sign and/or symptom, wherein the sign and/or symptom may at least one selected from the group consisting of: ocular debris, pouting of the meibomian glands, redness of the eyelid margin, swelling of the eyelid margin and ocular discomfort.

That is, in certain embodiments, the invention relates to a method according to the invention, wherein at the end of the treatment the subjects show a greater mean score improvement from baseline compared to a placebo/vehicle in ocular debris, pouting of the meibomian glands, redness of the eyelid margin, swelling of the eyelid margin or ocular discomfort.

In a particular embodiment, the invention relates to a composition for use according to the invention, wherein at the end of the treatment the subjects show a greater improvement from baseline compared to a placebo/vehicle in the mean score for swelling of the eyelid margin and ocular debris.

In a particular embodiment, the invention relates to a method according to the invention, wherein at the end of the treatment the subjects show a greater improvement from baseline compared to a placebo/vehicle in the mean score for swelling of the eyelid margin and ocular discomfort.

In a particular embodiment, the invention relates to a method according to the invention, wherein at the end of the treatment the subjects show a greater improvement from baseline compared to a placebo/vehicle in the mean score for ocular discomfort and ocular debris.

In a particular embodiment, the invention relates to a method according to the invention, wherein at the end of the treatment the subjects show a greater improvement from baseline compared to a placebo/vehicle in the mean score for swelling of the eyelid margin, ocular discomfort and ocular debris.

In a preferred embodiment, the invention relates to a method according to the invention, wherein at the end of the treatment the subjects show at least a 0.4 score unit greater improvement from baseline compared to a placebo/vehicle for the mean score for swelling of the eyelid margin (sign) and/or the mean score for ocular debris (sign) and an improvement compared to the placebo/vehicle for the mean score for ocular discomfort (symptom).

In a more preferred embodiment, the invention relates to a method according to the invention, wherein at the end of the treatment the subjects show at least a 0.4 score unit greater improvement from baseline compared to a placebo/vehicle for the mean score for swelling of the eyelid margin and/or the mean score for ocular debris (sign) and a greater improvement compared to the placebo/vehicle for the mean symptom score for ocular discomfort (symptom), wherein the treatment period is between 6 and 12 weeks, or, alternatively, wherein the treatment period is 2 weeks.

In an even more preferred embodiment, the invention relates to a method according to the invention, wherein at the end of the treatment the subjects show at least a 0.4 score unit greater improvement from baseline compared to a placebo/vehicle for the mean score for swelling of the eyelid margin and/or the mean score for ocular debris (signs) and a greater improvement compared to the placebo/vehicle for the mean score for ocular discomfort (symptom), wherein the treatment period is 6 or 12 weeks, or, alternatively, wherein the treatment period is 2 weeks.

In an even more preferred embodiment, the invention relates to a method according to the invention, wherein at the end of the treatment the subjects show at least a 0.4 score unit greater improvement from baseline compared to a placebo/vehicle for the mean score for swelling of the eyelid margin and/or the mean score for ocular debris (signs) and a greater improvement compared to the placebo/vehicle for the mean score for ocular discomfort (symptom), wherein the treatment period is between 6 and 12 weeks, or, alternatively, wherein the treatment period is 2 weeks, and wherein the composition is administered to the eyelid and/or the eyelid margin once, twice, three times or four times daily.

In an even more preferred embodiment, the invention relates to a method according to the invention, wherein at the end of the treatment the subjects show at least a 0.4 score unit greater improvement from baseline compared to a placebo/vehicle for the mean score for swelling of the eyelid margin and/or the mean score for ocular debris (signs) and a greater improvement compared to the placebo/vehicle for the mean score for ocular discomfort (symptom), wherein the treatment period is 6 or 12 weeks, or, alternatively, wherein the treatment period is 2 weeks, and wherein the composition is administered to the eyelid and/or the eyelid margin once, twice, three times or four times daily.

In a most preferred embodiment, the invention relates to a method according to the invention, wherein at the end of the treatment the subjects show at least a 0.4 score unit greater improvement from baseline compared to a placebo/vehicle for the mean score for swelling of the eyelid margin and/or the mean score for ocular debris (signs) and a greater improvement compared to the placebo/vehicle for the mean score for ocular discomfort (symptom), wherein the treatment period is 6 or 12 weeks, or, alternatively, wherein the treatment period is 2 weeks, and wherein the composition is administered to the eyelid and/or the eyelid margin twice daily.

In a particular embodiment, the invention relates to a method according to the invention, wherein at the end of the treatment the subjects show at least a 0.4 score unit greater improvement from baseline compared to a placebo/vehicle for the mean score for swelling of the eyelid margin and/or the mean score for ocular debris (signs) and at least a 10 mm greater improvement from baseline, in particular at least a 12, 13, 14 mm greater improvement from baseline, compared to the placebo/vehicle for the mean score for ocular discomfort (symptom), in particular wherein the treatment period is 6 or 12 weeks, or, alternatively, wherein the treatment period is 2 weeks, and wherein the composition is administered to the eyelid and/or the eyelid margin twice daily.

BRIEF DESCRIPTION OF FIGURES

FIG. 1: Structural formula of pimecrolimus

FIG. 2: Solubility of pimecrolimus in different solvents. The upper table shows the solubility of pimecrolimus in various organic and water-based solvents. Form B refers to the anhydrous, crystalline polymorph B of pimecrolimus that has been used in the manufacture of the composition according to the invention. The legend in the lower table defines the terms used for the categorization of solubility.

Figure 10:
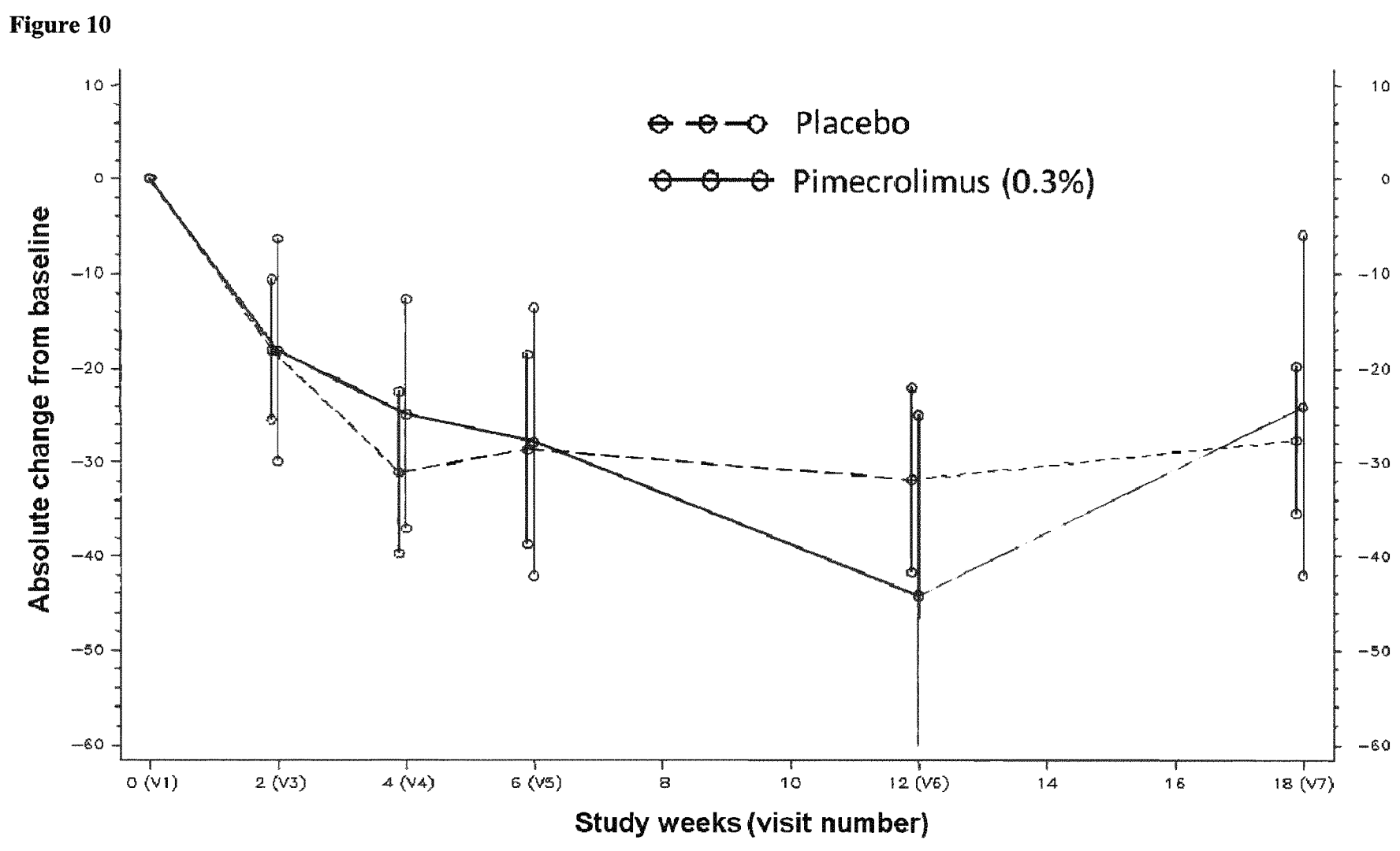

FIG. 10: The effect of an ointment comprising 0.3% pimecrolimus (solid line) on ocular discomfort of a non-target blepharitis population characterised by moderate to severe swelling or redness of the eyelid margin, pouting of the meibomian gland, ocular discomfort and in the absence of moderate to severe ocular debris. As a control, the effect of a placebo/vehicle control is shown (dashed line).

EXAMPLES

Example 1: Solubility of Pimecrolimus

Figure 1:
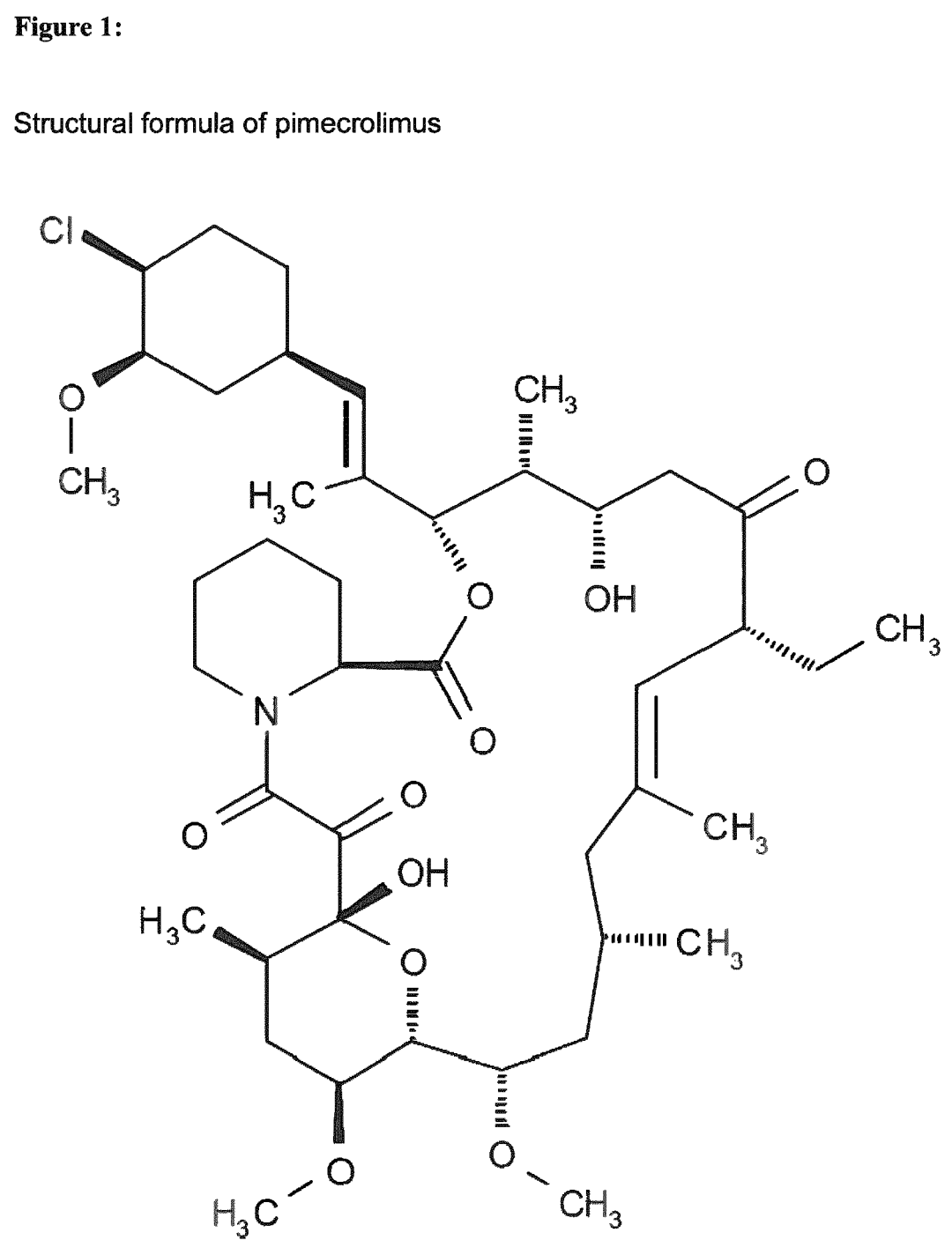
Figure 3:
FIG. 3: The effect of an ointment comprising 0.3% pimecrolimus (solid line) on the swelling of the eyelid margin of subjects from the entire study population. As a control, the effect of a placebo/vehicle control is shown (dashed line).

The active ingredient is pimecrolimus (FIG. 1). The IUPAC name of Pimecrolimus is: (1R,9S,12S,13R,14S,17R, 18E,21S,23S,24R,25S,27R)-12-[(1E)-2-{(1R,3R,4S)-4-chloro-3-methoxycyclohexyl}-1-methylvinyl]-17-ethyl-1, 14-dihydroxy-23,25-dimethoxy-13,19,21,27-tetramethyl-11,28-dioxa-4-aza-tricyclo[22.3.1.04,9]octacos-18-ene-2,3, 10,16-tetraone.

The solubility of pimecrolimus in different solvents was determined by HPLC after 24-hour equilibration (vibration) at 25.0+/−0.5° C. After the vibration, the precipitate was separated from the solution, dried and investigated by DSC and by X-ray diffraction pattern. The solubility of pimecrolimus in different solvents is summarized in FIG. 2. The results show that pimecrolimus is insoluble in aqueous solutions and water.

Example 2: Composition of the Dosage Form

TABLE 1

| Ingredient | Composition 1 Amount (mg/g) | Composition 2 Amount (mg/g) |
|---|---|---|
| Pimecrolimus | 3.0 | 1.0 |
| Triglycerides, medium-chain | 500.0 | 500.0 |
| Microcrystalline wax | 60.0 | 60.0 |
| Phenyl_ethyl alcohol | 10.0 | 10.0 |
| White Petrolatum | qs to 1.0 g | qs to 1.0 g |
| Total mass | 1.0 g | 1.0 g |

Excipients

All excipients utilized are pharmacopoeial excipients. Medium-chain triglycerides are used as solubilizer. Microcrystalline wax is added to improve the consistency and promote physical stability of the ointment. The content is optimized in order to prevent or minimize bleeding of medium-chain triglycerides from the ointment base as well as to keep an acceptable final consistency for patient acceptance. Phenyl ethyl alcohol is used as the preservative. A phenyl ethyl alcohol content of 1% is chosen for optimal preservative efficacy. The final product is tested for sterility according to the European Pharmacopoeia.

Example 3: Description of Production Process

1. Heat medium-chain triglycerides.
2. Mix in the pimecrolimus drug substance until dissolved.
3. Add microcrystalline wax, white petrolatum and optionally phenyl ethyl alcohol and dissolve under stirring.
4. Filter the ointment.
5. The filtered bulk ointment will be mixed and cooled to room temperature gradually, with temperature, time, and mixing speed documented for process.

Example 4

The following examples describe a randomized, double blind, placebo/vehicle-controlled evaluation of the safety and efficacy of pimecrolimus ophthalmic ointment used twice a day in subjects diagnosed with blepharitis.

The objective of this study was to compare the efficacy of pimecrolimus 0.3% ophthalmic ointment used twice a day to that of placebo/vehicle (PL) used twice a day for the treatment of blepharitis.

A clinical trial was carried out designed to identify treatment effects of a size of 0.4 score units/10 mm in terms of statistical trends (one-side alpha level of 0.1) [i.e. p value of <0.2 predetermined to be indicative of a trend]. Such differences were deemed to be clinically meaningful (subsequently confirmed by EU regulatory authorities in DK & SE in 2005).

Study Design

The study was carried out as a double blind, placebo/vehicle-controlled, parallel-group, multi-center study, and has a randomized design with a 1:1 allocation ratio of 98 patients, with a primary readout at 12 weeks followed by a 6-week follow-up period off-drug.

Efficacy Assessments Signs

Change from baseline in the severity of ocular debris as assessed by slit-lamp examination (0-4 scale)

Change from baseline in severity of pouting of the meibomian gland (0-4 scale)

Change from baseline in severity of redness of the eyelid margin (0-4 scale)

Change from baseline in severity of swelling of the eyelid margin (0-4 scale)

Change from baseline in character of secretion expressed (0-3 scale)

Change from baseline in corneal and conjunctival staining scores (Oxford Grading Scheme 0-5 scale)

Signs (interpreted from photographs by a central reading centre); Ocular debris (0-4 scale), Redness of the eyelid margin (0-4 scale), Swelling of the eyelid margin (0-4 scale), Pouting of the meibomian gland (0-4 scale).

Ocular Debris (Collarettes, Crusting/Scaling, Tear-Film Debris)

The investigator rated the severity of signs according to the following classification:

(0) Normal clear eyelid margin
(1) Mild occasional fragment, 1-5 collarettes
(2) Moderate few fragments, 6-20 collarettes
(3) Severe many fragments, 21-40 collarettes
(4) Very severe clumps/strands, >40 collarettes Redness of the Eyelid Margin The investigator rated the severity of signs according to the following classification:

(0) Normal no redness.
(1) Mild slightly dilated blood vessels; vessels colored pink; present in a segment of the eyelid margin.
(2) Moderate more apparent dilation of blood vessels; vessel color more intense, whole margin of the eyelid is involved.
(3) Severe increased vascularity of the eyelid margin, numerous and obvious dilated blood vessels, deep red in color, whole margin of the eyelid is involved.
(4) Very severe clearly increased vascularity of the eyelid margin, large, numerous dilated blood vessels characterised by deep red color, whole margin of the eyelid is involved, noticeable conjunctival hyperemia.

Swelling of the Eyelid Margin

The investigator rated the severity of signs according to the following classification:

(0) Normal no swelling of the eyelid tissue.
(1) Mild some swelling of the eyelid margin.
(2) Moderate diffuse swelling of the eyelid margin.
(3) Severe severe swelling of the eyelid margin with alterations in the eyelid folds.
(4) Very severe swelling which clearly reduces interpalpebral aperture.

Pouting of the Meibomian Gland

The investigator rated the severity of signs according to the following classification:

(0) Normal clear orifices of meibomian glands.
(1) Mild less than 1/3 of orifices contain turbid or oily secretions.
(2) Moderate between 1/3 and 2/3 of orifices contain turbid or oily secretions.
(3) Severe more than 2/3 of orifices contain turbid or oily secretions.
(4) Very severe any occlusion and/or engorgement of meibomian glands, formation of cysts, thickening, rounding, notching of the eyelid.

Efficacy Assessment of Symptoms

Change from baseline in the severity of ocular discomfort as assessed by the patient (worst symptom at baseline, visual analogue scale)

Change from baseline in severity of ocular symptoms of blepharitis, i.e. foreign body sensation, itching, dryness, burning/pain (0-4 scale), swollen/heavy eyelids (0-3 scale)

Ocular Discomfort

Ocular discomfort was assessed by the patient using a visual analogue scale. At the initial visit (week 0), the symptom which causes the most ocular discomfort was identified as the "worst symptom at baseline".

At Week 0:

What has been the patient's worst symptom (i.e., the one that causes the most ocular discomfort) over the past 2 weeks? Please make a mark on the scale below to indicate how your eyes have felt over the past 2 weeks.

At Weeks 2, 4, 6 and 12:

Your worst symptom at the beginning of the study was . . . (verbal reminder from site staff). Please make a mark on the scale below to indicate how your eyes have felt since the last visit The scales for all visits are printed on the same data collection sheet, so patients are able to see what their prior rating was. The staff should, however, not prompt the patients in this regard. The level of discomfort is measured by site staff to the nearest millimeter from the left side of the scale to the mark made by the patient.

Main Efficacy Endpoints:

the absolute change from baseline to week 12 in redness of the eyelid margin (0-4 scale).

the absolute change from baseline to week 12 in swelling of the eyelid margin (0-4 scale).

the absolute change from baseline to week 12 in ocular discomfort (0-100 mm visual analogue scale).

Example 5: Population 1—all Patients (Per Protocol)

Main Inclusion Criteria

Patients with a clinical diagnosis of blepharitis for at least three months, failing lid hygiene who fulfilled in at least one eye (the same eye) the following criteria:

score of at least 2 (moderate) on either redness OR swelling (or both) of the eyelid margin score of at least 2 (moderate) on either ocular debris OR pouting of the meibomian gland (or both)

score of at least 40 mm (moderate) on ocular discomfort (worst symptom at baseline) AND a score of at least 2 (moderate) on any one symptom

TABLE 2

| Subject disposition (safety population) | | |
| --- | --- | --- |
| | Composition 1 (0.3% pimecrolimus) n (%) | Placebo/vehicle n (%) |
| Total no. of subjects n(%) | | |
| Screened | 100 | |
| Enrolled | 98 | |
| Randomized | 48 (100) | 50 (100) |
| Exposed | 48 (100) | 50 (100) |
| Completed | 38 (79) | 45 (90) |
| Discontinuations - n(%) | | |
| Total | 10 (21) | 5 (10) |
| Adverse events | 8 (17) | 3 (6) |
| Unsatisfactory therapeutic effect | 2 (4) | 2 (4) |

Swelling of Eyelid Margin

The effect of Composition 1 on the swelling of the eyelid margin is summarized in FIG. 3 and Table 3. Patients that were treated with Composition 1 comprising 0.3% pimecrolimus showed reduced swelling of the eyelid margin compared to patients treated with a placebo/vehicle.

TABLE 3

| Swelling of eyelid margin at Week 12 (worse eye, PP/moderate/severe population) | | | |
| --- | --- | --- | --- |
| Swelling of eyelid margin (0-4 scale*) | Composition 1 (0.3% pimecrolimus) (N = 37/34) | Placebo/ vehicle (N = 44/35) | Composition 1 – Placebo/vehicle Diff[90% CI]***, P-Value** |
| All: | | | |
| Mean absolute value at baseline (BL) | 2.30 | 2.14 | −0.26 (−0.63, 0.12) P = 0.2789 |
| Mean absolute change from BL +/− SD | −1.05 +/− 0.94 (n = 37) | −0.80 +/− 1.07 (n = 44) | |
| Baseline >= 2: | | | |
| Mean absolute value at BL | 2.44 | 2.57 | −0.20 (−0.62, 0.21) P = 0.1849 |
| Mean absolute change from BL +/− SD | −1.15 +/− 0.93 (n = 34) | −0.94 +/− 1.11 (n = 35) | |

*Grades 0-4: none, mild, moderate, severe, very severe.

**baseline stratified 2-sided Cochran-Mantel-Haenszel (CMH)-test (table scores).

***based on normal distribution

Ocular Discomfort

Figure 4:
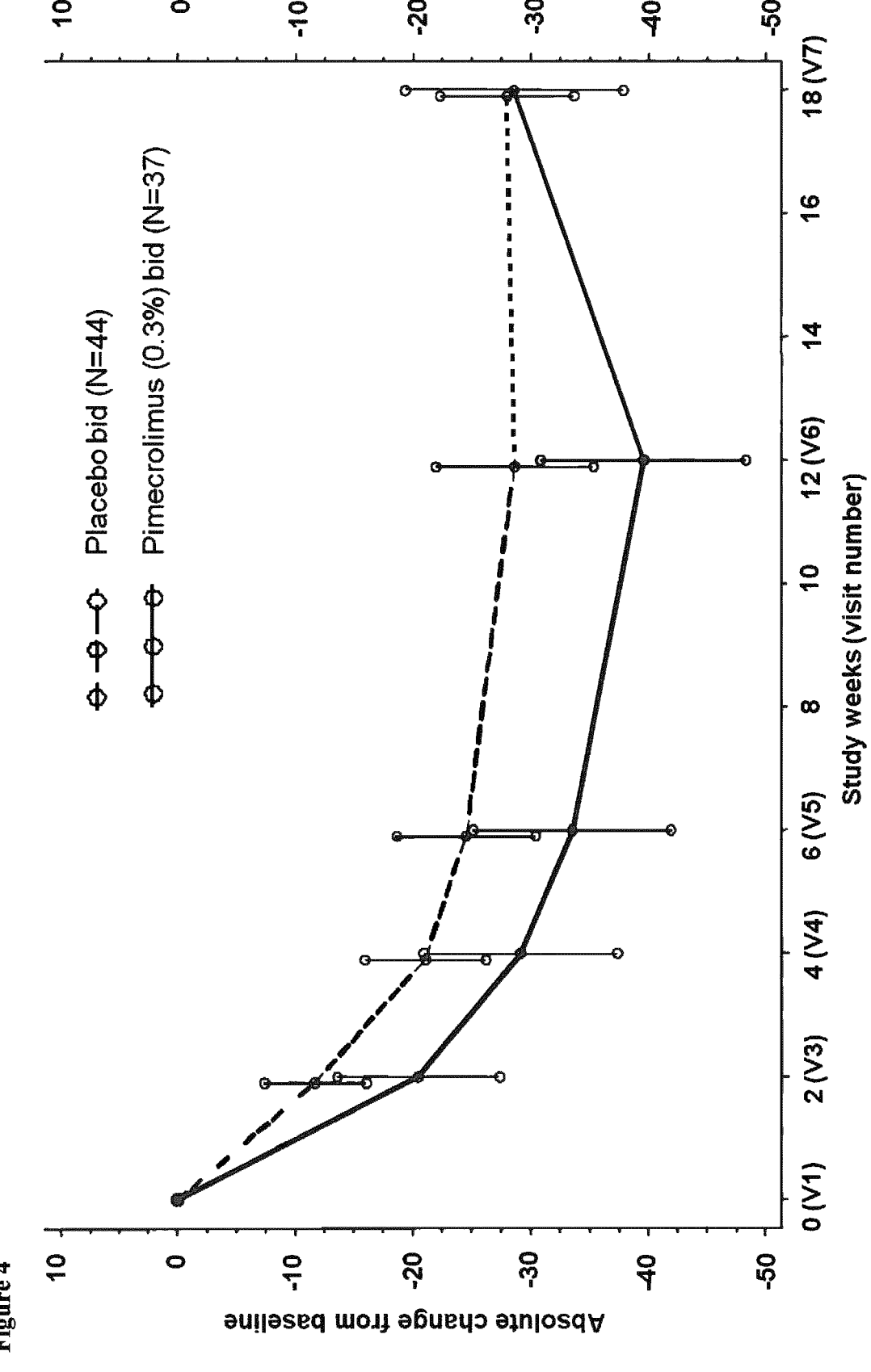
FIG. 4: The effect of an ointment comprising 0.3% pimecrolimus (solid line) on ocular discomfort of subjects from the entire study population. As a control, the effect of a placebo/vehicle control is shown (dashed line).

The effect of Composition 1 on ocular discomfort is summarized in FIG. 4 and Table 4. Patients that were treated with Composition 1 comprising 0.3% pimecrolimus showed reduced ocular discomfort compared to patients treated with a placebo/vehicle.

TABLE 4

| Ocular discomfort at week 12 (worse eye, PP) | | | |
| --- | --- | --- | --- |
| Ocular discomfort (0-100 mm visual analogue scale*) | Composition 1 (0.3% pimecrolimus) (N = 37) | Placebo/ vehicle (N = 44) | Composition 1 – Placebo/vehicle Diff[90% CI]**, P-Value** |
| | All: | | |
| Mean absolute value at BL | 72.7 | 68.2 | −10.9 (−21.6, −0.3) P = 0.0924 |
| Mean absolute change from BL +/− SD | −39.6 +/− 31.5 | −28.7 +/− 26.3 | |

*Worst symptom at baseline

**t-test

Adverse Events

Tables 5 and 6 disclose that patients treated with composition 1 comprising 0.3% pimecrolimus did not report significantly more adverse events than patients treated with a placebo/vehicle. The most common adverse event was eye irritation, which was observed in patients treated with Composition 1 comprising 0.3% pimecrolimus and patients treated with a placebo/vehicle at comparable rates.

TABLE 5

Number of patients with adverse events
(safety population, treatment phase)

| | Composition 1 (0.3% pimecrolimus) (N = 48) | | Placebo/vehicle (N = 50) | |
|---|---|---|---|---|
| Totals | n | % | n | % |
| Number of patients with at least one event | 32 | (67) | 34 | (68) |
| Number of patients with at least one non-ocular event | 7 | (15) | 10 | (20) |
| Number of patients with at least one ocular event | 31 | (65) | 30 | (60) |

TABLE 6

Number of patients with most frequent AEs
(safety population, treatment phase)

| | | Composition 1 (0.3% pimecrolimus) (N = 48) | | Placebo/vehicle (N = 50) | |
|---|---|---|---|---|---|
| | | n | % | n | % |
| Totals | Total with at least 1 AE | 32 | (67) | 34 | (68) |
| Eye disorders | Abnormal sensation in eye | 3 | (6) | 0 | (0) |
| | Blepharitis | 1 | (2) | 3 | (6) |
| | Conjunctival disorder | 0 | (0) | 3 | (6) |
| | Corneal disorder | 0 | (0) | 2 | (4) |
| | Erythema of eyelid | 2 | (4) | 1 | (2) |
| | Eye irritation | 19 | (40) | 16 | (32) |
| | Eye pruritus | 2 | (4) | 2 | (4) |
| | Eye redness | 3 | (6) | 0 | (0) |
| | Eyelid irritation | 2 | (4) | 2 | (4) |
| | Eyelid oedema | 2 | (4) | 0 | (0) |
| | Lacrimation increased | 5 | (10) | 0 | (0) |
| | Vision blurred | 4 | (8) | 4 | (8) |
| Infections and infestations | Nasopharyngitis | 0 | (0) | 3 | (6) |
| Muscoskeletal and connective tissue disorders | Arthralgia | 0 | (0) | 2 | (4) |

Example 6: Population 2—Blepharitis Characterised by Swelling and/or Redness of the Eyelid Margin, Ocular Debris and Ocular Discomfort Main Inclusion Criteria Patients with a clinical diagnosis of blepharitis for at least three months, failing lid hygiene who fulfilled in at least one eye (the same eye) the following criteria:

score of at least 2 (moderate) on either redness OR swelling (or both) of the eyelid margin score of at least 2 (moderate) on ocular debris score of at least 40 mm (moderate) on ocular discomfort (worst symptom at baseline) AND a score of at least 2 (moderate) on any one symptom

TABLE 7

Patient disposition

| | Composition 1 (0.3% pimecrolimus) | | Placebo/vehicle | |
|---|---|---|---|---|
| Total no. of patients n(%) | | | | |
| Screened | 100 | | | |
| Randomized | 35 | (100) | 29 | (100) |
| Exposed | 35 | (100) | 29 | (100) |
| Completed | 28 | (80) | 25 | (86) |
| Discontinuations | 7 | (20) | 4 | (14) |
| Discontinuations - n(%) | | | | |
| Adverse events | 5 | (14) | 3 | (10) |
| Unsatisfactory therapeutic effect | 2 | (6) | 1 | (3) |

Swelling of Eyelid Margin

Figure 5:
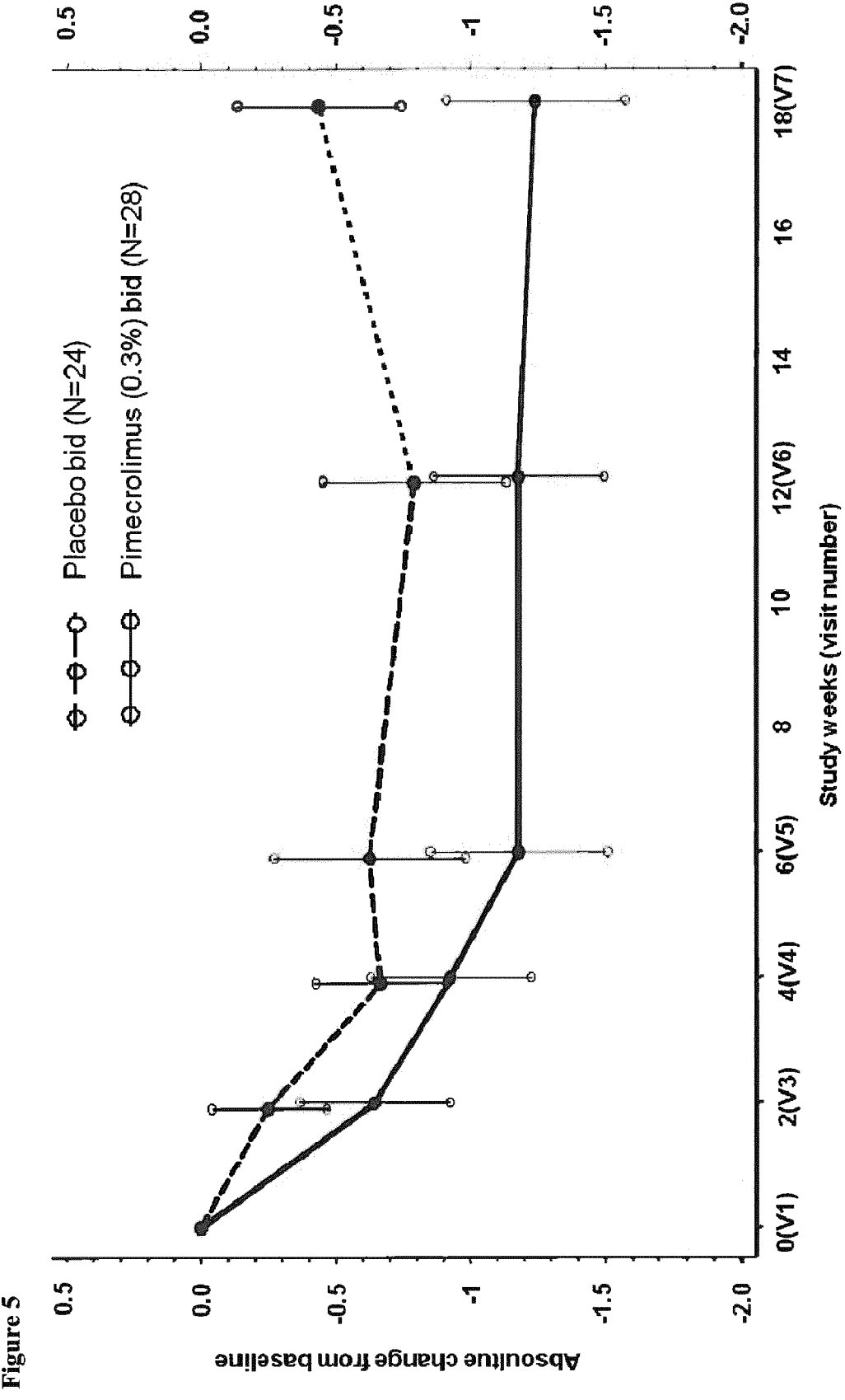
FIG. 5: The effect of an ointment comprising 0.3% pimecrolimus (solid line) on the swelling of the eyelid margin of a blepharitis population (characterised by moderate to severe swelling OR redness of the eyelid margin, ocular debris and ocular discomfort). As a control, the effect of a placebo/vehicle control is shown (dashed line).

The effect of Composition 1 on the swelling of the eyelid margin is summarized in FIG. 5 and Table 8. Patients that were treated with Composition 1 comprising 0.3% pimecrolimus showed significantly reduced swelling of the eyelid margin compared to patients treated with a placebo/vehicle. It was surprisingly found that patients suffering from moderate to severe blepharitis (baseline>=2) showed a mean improvement from baseline compared to placebo/vehicle of 0.51.

TABLE 8

Swelling of eyelid margin at Week 12

| Swelling of eyelid margin (0-4 scale*) | Composition 1 (0.3% pimecrolimus) (N = 28/25) | Placebo/ vehicle (N = 24/21) | Composition 1 – Placebo/vehicle Diff[90% CI]***, P-Value** |
|---|---|---|---|
| All: | | | |
| Mean absolute value at BL | 2.32 | 2.29 | −0.39 (−0.84, 0.07) P = 0.1688 |
| Mean absolute change from BL +/− SD | −1.18 +/− 0.98 (n = 28) | −0.79 +/− 0.98 (n = 24) | |
| Baseline >= 2: | | | |
| Mean absolute value at BL | 2.52 | 2.48 | −0.51 (−1.00, −0.02) P = 0.0847 |
| Mean absolute change from BL +/− SD | −1.32 +/− 0.95 (n = 25) | −0.81 +/− 1.03 (n = 21) | |

Figure 6:
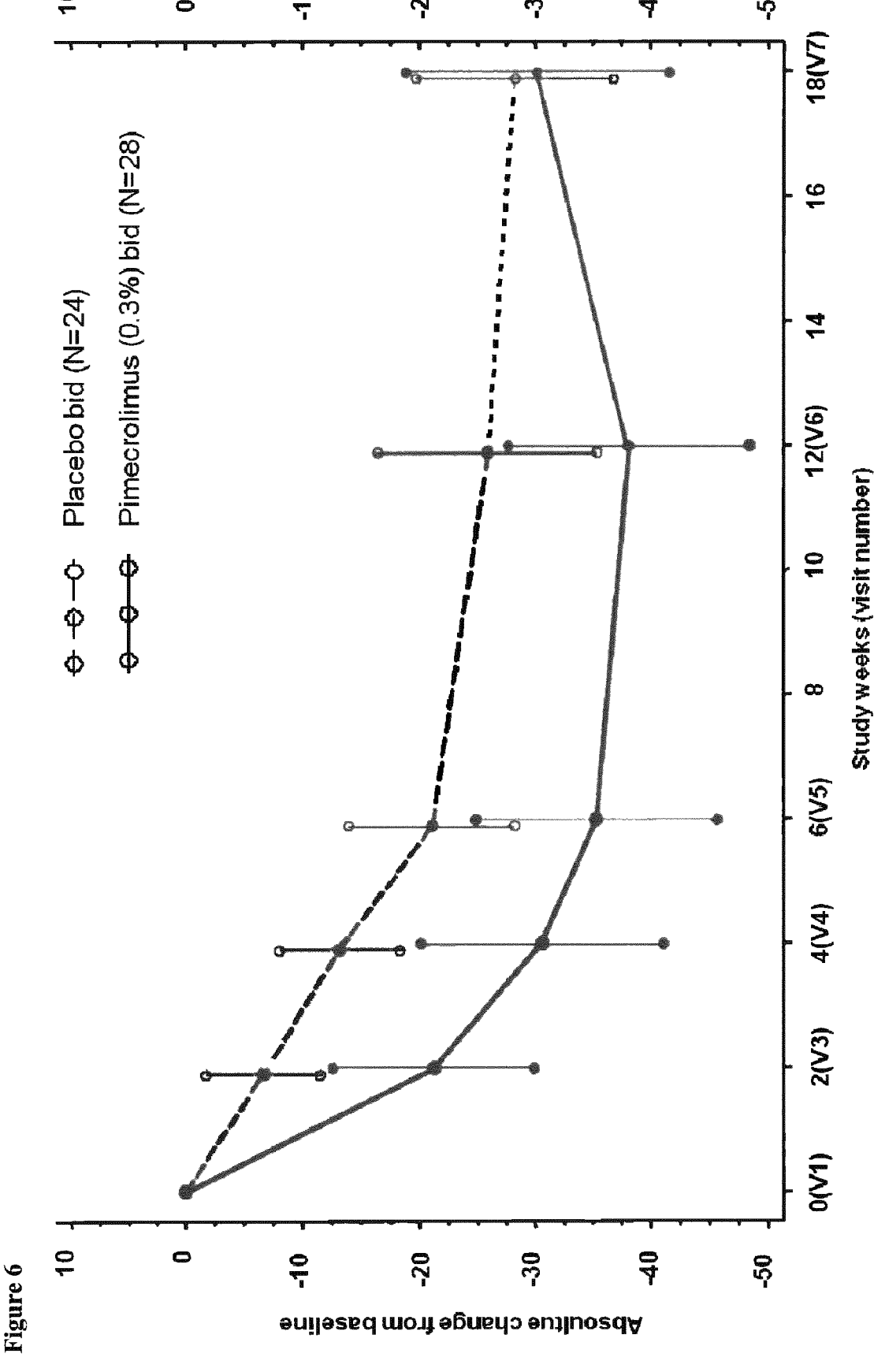
FIG. 6: The effect of an ointment comprising 0.3% pimecrolimus (solid line) on ocular discomfort of a blepharitis population (characterised by moderate to severe swelling OR redness of the eyelid margin, ocular debris and ocular discomfort). As a control, the effect of a placebo/vehicle control is shown (dashed line).

*Grades 0-4: none, mild, moderate, severe, very severe.
**baseline stratified 2-sided Cochran-Mantel-Haenszel (CMH)-test (table scores).
***based on normal distribution Ocular Discomfort The effect of Composition 1 on ocular discomfort is summarized in FIG. 6 and Table 9 Patients that were treated with Composition 1 comprising 0.3% pimecrolimus showed significantly reduced ocular discomfort compared to patients treated with a placebo/vehicle.

TABLE 9

Ocular discomfort at week 12

| Ocular discomfort (0-100 mm visual analogue scale*) | Composition 1 (0.3% pimecrolimus) (N = 28) | Placebo/ vehicle (N = 24) | Composition 1 – Placebo/vehicle Diff[90% CI]**, P-Value** |
|---|---|---|---|
| All: | | | |
| Mean absolute value at BL | 72.9 | 74.3 | −12.1 (−21.6,−0.3) P = 0.1509 |

TABLE 9-continued

| Ocular discomfort at week 12 | | | |
|---|---|---|---|
| Ocular discomfort (0-100 mm visual analogue scale*) | Composition 1 (0.3% pimecrolimus) (N = 28) | Placebo/ vehicle (N = 24) | Composition 1 – Placebo/vehicle Diff[90% CI]**, P-Value** |
| | | All: | |
| Mean absolute change from BL +/– SD | −38.1 +/− 32.1 (n = 28) | −26.0 +/− 27.1 (n = 24) | |

*Worst symptom at baseline
**t-test

Adverse Events

Tables 10 and 11 disclose that patients treated with composition 1 comprising 0.3% pimecrolimus did not report significantly more adverse events than patients treated with a placebo/vehicle. The most common adverse event was eye irritation, which was observed in patients treated with Composition 1 comprising 0.3% pimecrolimus and patients treated with a placebo/vehicle at comparable rates.

TABLE 10

| Number of patients with adverse events (safety population, treatment phase) | | | | |
|---|---|---|---|---|
| | Composition 1 (0.3% pimecrolimus) (N = 35) | | Placebo/ vehicle (N = 29) | |
| Totals | n | % | n | % |
| Number of patients with at least one event | 21 | (60) | 16 | (55) |
| Number of patients with at least one non-ocular event | 5 | (14) | 5 | (17) |
| Number of patients with at least one ocular event | 20 | (57) | 15 | (52) |

TABLE 11

| Number of patients with most frequent AEs (safety population, treatment phase) | | | | | |
|---|---|---|---|---|---|
| | | Composition 1 (0.3% pimecrolimus) (N = 35) | | Placebo/ vehicle (N = 29) | |
| | | n | % | n | % |
| Totals | Total with at least 1 AE | 21 | (60) | 16 | (55) |
| Eye disorders | Eyelid irritation | 2 | (6) | 2 | (7) |
| | Eye irritation | 10 | (29) | 16 | (24) |
| | Eyelid oedema | 2 | (6) | 3 | (0) |
| | Foreign body sensation in eyes | 2 | (6) | 2 | (0) |
| | Lacrimation increased | 3 | (9) | 1 | (0) |
| | Ocular hyperaemia | 2 | (6) | | (0) |
| | Vision blurred | 2 | (6) | 4 | (10) |
| Infections and infestations | Nasopharyngitis | 0 | (0) | 3 | (7) |

Figure 7:
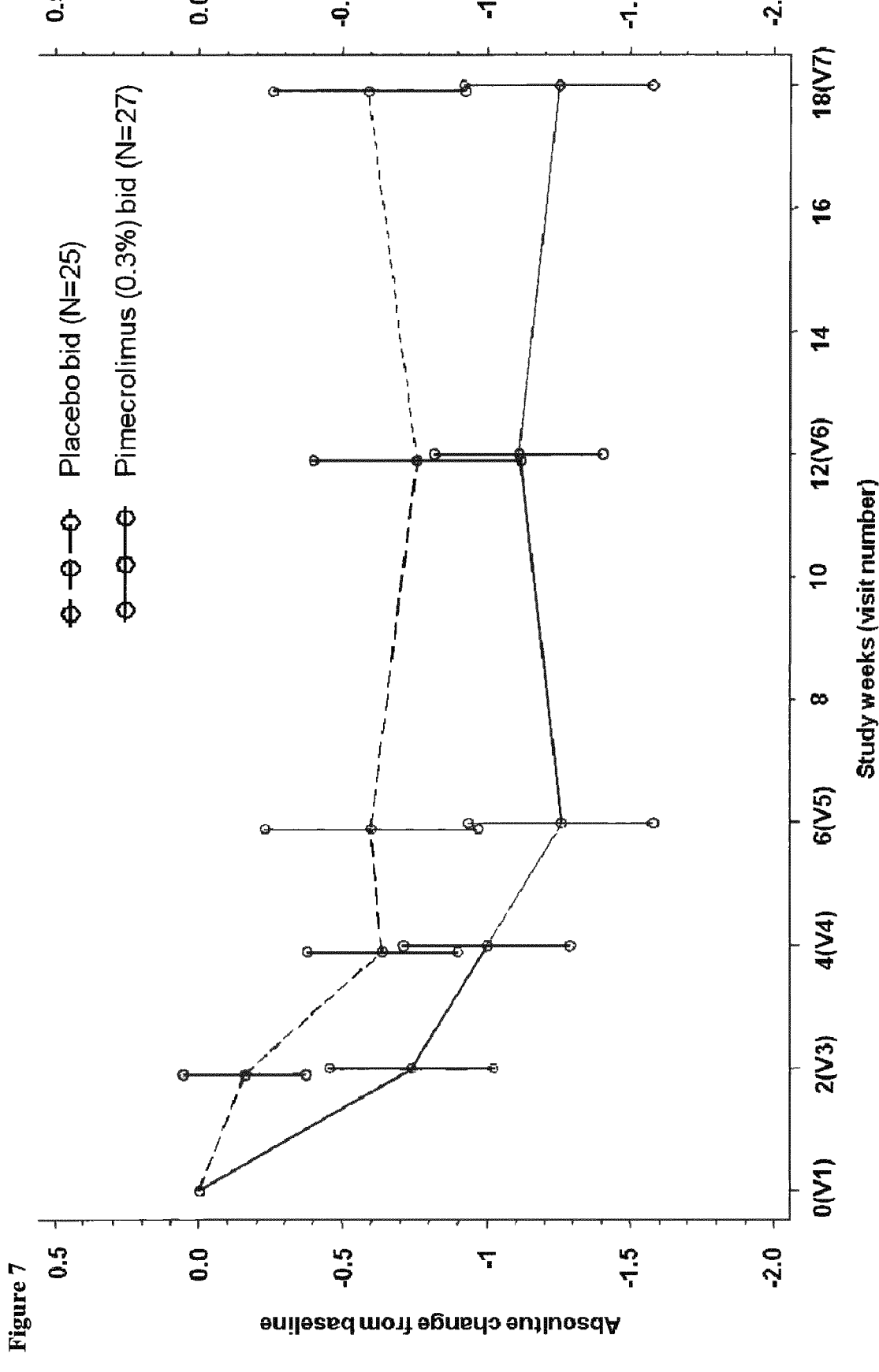
FIG. 7: The effect of an ointment comprising 0.3% pimecrolimus (solid line) on the swelling of the eyelid margin of the target blepharitis population, characterised by moderate to severe swelling of the eyelid margin, ocular debris and ocular discomfort. As a control, the effect of a placebo/vehicle control is shown (dashed line).
Figure 8:
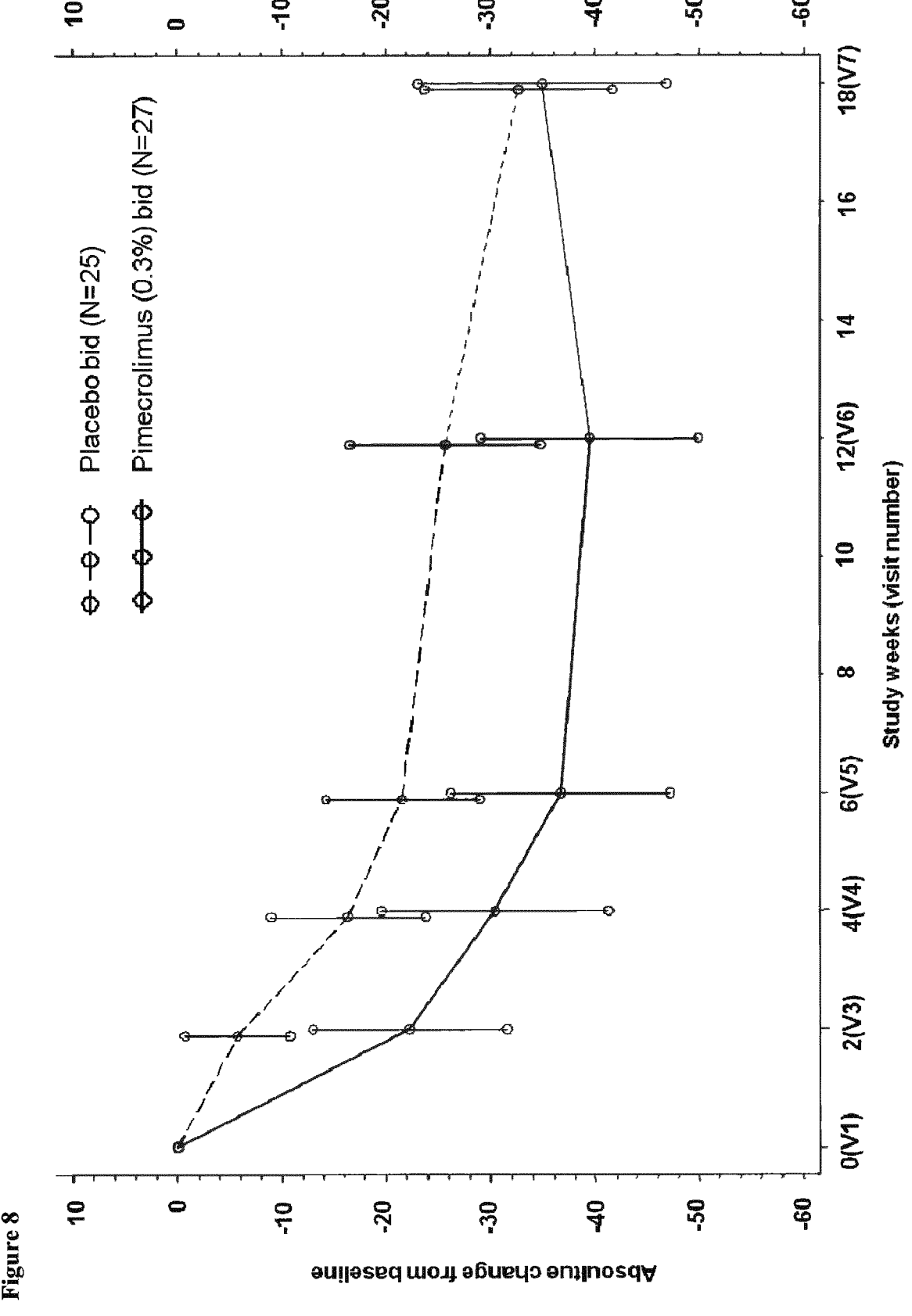
FIG. 8: The effect of an ointment comprising 0.3% pimecrolimus (solid line) on ocular discomfort of the target blepharitis population, characterised by moderate to severe swelling of the eyelid margin, ocular debris and ocular discomfort. As a control, the effect of a placebo/vehicle control is shown (dashed line).

Example 7: Population 3 (Target Population)—Moderate to Severe Blepharitis Characterised by Swelling of the Eyelid Margin, Ocular Debris and Ocular Discomfort Main Inclusion Criteria Patients with a clinical diagnosis of blepharitis for at least three months, failing lid hygiene who fulfilled in at least one eye (the same eye) the following criteria:

score of at least 2 (moderate) on swelling of the eyelid margin score of at least 2 (moderate) on ocular debris score of at least 40 mm (moderate) on ocular discomfort (worst symptom at baseline) AND a score of at least 2 (moderate) on any one symptom Outcome of Treatment Patients treated with Composition 1 comprising 0.3% pimecrolimus showed significantly reduced swelling of the eyelid margin and significantly reduced ocular discomfort compared to patients treated with a placebo/vehicle (see FIGS. 7 and 8).

Figure 9:
FIG. 9: The effect of an ointment comprising 0.3% pimecrolimus (solid line) on the swelling of the eyelid margin of a non-target blepharitis population characterised by moderate to severe swelling OR redness of the eyelid margin, pouting of the meibomian gland, ocular discomfort and in the absence of moderate to severe ocular debris. As a control, the effect of a placebo/vehicle control is shown (dashed line).

Example 8: Population 4—Blepharitis Characterised by Moderate to Severe Swelling and/or Redness of the Eyelid Margin, Pouting of the Meibomian Gland, Ocular Discomfort and in the Absence of Moderate to Severe Ocular Debris Main Inclusion Criteria Patients with a clinical diagnosis of blepharitis for at least three months, failing lid hygiene who fulfilled in at least one eye (the same eye) the following criteria:

score of at least 2 (moderate) on either redness OR swelling (or both) of the eyelid margin score of <2 (none/mild) on ocular debris AND at least 2 (moderate on pouting of the meibomian gland score of at least 40 mm (moderate) on ocular discomfort (worst symptom at baseline) AND a score of at least 2 (moderate) on any one symptom Outcome of Treatment Patients from the above-mentioned patient group reported no significant reduction in the swelling of the eyelid margin and no clear improvement of ocular discomfort (see FIGS. 9 and 10).

REFERENCES

1. Lindsley, K., Interventions for chronic blepharitis, 2012, Cochrane Database Syst Rev, 16(5), CD005556.
2. Dougherty, J. M. and McCulley, J. P., Comparative bacteriology of chronic blepharitis, 1984, Br J Ophthalmol, 68(8), 524-8.
3. McCulley, J. Blepharoconjunctivitis, 1984, Int Ophthalmol Clin, 24(2), 65-77.
4. Meingassner, J. G., et al., A novel anti-inflammatory drug, SDZ ASM 981, for the topical and oral treatment of skin diseases: in vivo pharmacology, 1997, Br J Dermatol, 137(4), 568-576.
5. Zuberbier, T., et al., The ascomycin macrolactam pimecrolimus (Elidel, SDZ ASM 981) is a potent inhibitor of mediator release from human dermal mast cells and peripheral blood basophils, 2001, J Allergy Clin Immunol, 108(2), 275-280.
6. Luger, T., et al., SDZ ASM 981: an emerging safe and effective treatment for atopic dermatitis, 2001, Br J Dermatol, 144(4), 788-794.

7. Meingassner, J. G., et al., Pimecrolimus inhibits the elicitation phase but does not suppress the sensitization phase in murine contact hypersensitivity, in contrast to tacrolimus and cyclosporine A, 2003, J Invest Dermatol, 121(1), 77-80.

8. Kiiski, V., et al., Long-term Safety of Topical Pimecrolimus and Topical Tacrolimus in Atopic Blepharoconjunctivitis, 2014, JAMA Dermatol, 150(5), 571-573.

9. Auw-Hädrich, C. and Reinhard, T., Therapeutische Optionen bei chronischer Blepharitis unter Berücksichtigung der Evidenzlage, 2016, Der Ophtamologe, 113(12), 1082-1085.

10. Gaynor, B. D., et al., Topical ocular antibiotics induce bacterial resistance at extraocular sites, 2005, Br J Ophthalmol, 89(9), 1097-1099.

11. Auw-Hädrich, C. and Reinhard, T., Behandlung der chronischen Blepharokeratokonjunktivitis mit lokalen Kalzineurininhibitoren, 2009, Opthamologe, 106, 635-638.

12. Ousler III, G. W. et al., Evaluation of pimecrolimus 1%, 0.3% and 0.1% compared to vehicle for the treatment of dry eye in the controlled adverse environment (CAE) model, 2005, The Occular Surface, 3(1), S99.

13. Rynerson, J. M. and Perry, H. D., DEBS—a unification theory of dry eye and blepharitis, 2016, Clinical Ophthamology, 10, 2455-2467.

14. Nelson, J. D. et al. TFOS DEWS II Introduction, 2017, The Ocular Surface 15, 269-275

15. Lemp, M. A. and Kelly, K. N., Blepharitis in the United States 2009: A Survey-based Perspective on Prevalence and Treatment, 2009, The Ocular Surface, 7(2), S1

The invention claimed is:

1. A method of treating a patient having moderate to severe blepharitis, the method comprising administering to said patient a composition comprising between 0.05% (wt/wt) and 0.6% (wt/wt) pimecrolimus;

wherein said patient has the following signs and symptoms of moderate to severe blepharitis:

(i) a score of at least 2 on swelling of the eyelid margin on a 0-4 scale;

(ii) a score of at least 2 on ocular debris on a 0-4 scale; and (iii) a symptom score of at least 40 mm on ocular discomfort on a 100 mm visual analogue scale.

2. The method according to claim 1, wherein the composition is administered to the eyelid and/or eyelid margin of said patient.

3. The method according to claim 2, wherein a unit dosage of the composition is administered once, twice, three times, or four times a day.

4. The method according to claim 1, wherein said composition comprises between 0.1% (wt/wt) and 0.4% (wt/wt) pimecrolimus.

5. The method according to claim 4, wherein said composition comprises 0.3% (wt/wt) pimecrolimus.

6. The method according to claim 1, wherein said composition is formulated as an ointment having an ointment base selected from ophthalmically acceptable oil and fat bases.

7. The method according to claim 6, wherein said composition further comprises a medium-chain triglyceride and a microcrystalline wax.

8. The method according to claim 7, wherein said medium-chain triglyceride is present in an amount between 30% (wt/wt) and 60% (wt/wt).

9. The method according to claim 8, wherein said medium-chain triglyceride comprises caprylic and/or capric acid.

10. The method according to claim 7, wherein said microcrystalline wax is present in an amount between 3% (wt/wt) and 10% (wt/wt).

11. The method according to claim 7, wherein said composition comprises 0.3% (wt/wt) pimecrolimus, 50% (wt/wt) medium-chain triglyceride, and 6% (wt/wt) microcrystalline wax.

12. The method according to claim 11, wherein a unit dosage of said composition is administered twice a day.

13. The method according to claim 3, wherein said treatment is carried out for at least 2 weeks.

14. A method of treating a patient having chronic blepharitis, which comprises administering to the eyelid and/or eyelid margin of said patient a composition comprising between 0.1% (wt/wt) and 0.4% (wt/wt) of pimecrolimus;

wherein said blepharitis is moderate to severe blepharitis such that the patient has:

(i) a score of at least 2 on swelling of the eyelid margin on a 0-4 scale;

(ii) a score of at least 2 on ocular debris on a 0-4 scale; and (iii) a symptom score of at least 40 mm on ocular discomfort on a 100 mm visual analogue scale.

15. The method according to claim 14, wherein said composition is administered once, twice, three times, or four times per day.

16. The method according to claim 15, wherein said treatment is carried out for at least 2 weeks.

* * * * *